(12) United States Patent
Straub et al.

(10) Patent No.: US 11,415,581 B2
(45) Date of Patent: *Aug. 16, 2022

(54) METHOD OF TREATING SOLID CANCERS AND/OR METASTASES THEREOF WITH PAN AV INTEGRIN INHIBITOR, MEDICAMENTS THEREFORE, AND A METHOD OF PREDICTING THE CLINICAL OUTCOME OF TREATING SOLID CANCERS AND/OR METASTASES THEREOF

(71) Applicant: Merck Patent GmbH, Darmstadt (DE)

(72) Inventors: Josef Straub, Seeheim-Jugenheim (DE); Eike Staub, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/511,993

(22) PCT Filed: Aug. 18, 2015

(86) PCT No.: PCT/EP2015/001699
§ 371 (c)(1),
(2) Date: Mar. 16, 2017

(87) PCT Pub. No.: WO2016/041614
PCT Pub. Date: Mar. 24, 2016

(65) Prior Publication Data
US 2017/0298134 A1    Oct. 19, 2017

Related U.S. Application Data

(60) Provisional application No. 62/051,530, filed on Sep. 17, 2014.

(51) Int. Cl.
| | | |
|---|---|---|
| *G01N 33/574* | (2006.01) | |
| *A61K 39/395* | (2006.01) | |
| *A61K 31/4745* | (2006.01) | |
| *C07K 16/28* | (2006.01) | |
| *A61K 39/00* | (2006.01) | |

(52) U.S. Cl.
CPC ... *G01N 33/57419* (2013.01); *A61K 31/4745* (2013.01); *A61K 39/39558* (2013.01); *C07K 16/2848* (2013.01); *C07K 16/2863* (2013.01); *G01N 33/574* (2013.01); *G01N 33/57488* (2013.01); *A61K 2039/505* (2013.01); *C07K 2317/24* (2013.01); *G01N 2333/47* (2013.01); *G01N 2800/52* (2013.01)

(58) Field of Classification Search
CPC . G01N 33/57484; G01N 33/574; G01N 33/68
See application file for complete search history.

(56) References Cited

U.S. PATENT DOCUMENTS

| | | |
|---|---|---|
| 5,985,278 A | 11/1999 | Mitjans et al. |
| 7,163,681 B2 | 1/2007 | Giles-Komar et al. |
| 8,562,986 B2 | 10/2013 | Goodman et al. |
| 2005/0159361 A1 | 7/2005 | Hara et al. |
| 2007/0117164 A1 | 5/2007 | Raskov et al. |
| 2007/0269824 A1* | 11/2007 | Albrecht ............... C12Q 1/00 435/6.11 |
| 2010/0254977 A1* | 10/2010 | Goodman ........ A61K 39/3955 424/133.1 |
| 2019/0338037 A1 | 11/2019 | Straub et al. |

FOREIGN PATENT DOCUMENTS

| | | |
|---|---|---|
| CN | 102265156 A | 11/2011 |
| EP | 0 531 472 B1 | 3/1993 |
| EP | 0719 859 A1 | 7/1996 |
| JP | 2004-002321 | 1/2004 |
| JP | 2004-510414 | 4/2004 |
| JP | 2004-528340 | 9/2004 |
| JP | 2012-513422 | 6/2012 |
| JP | 2013-505436 | 2/2013 |
| JP | 2014-510047 | 4/2014 |
| WO | 2002/12501 A2 | 2/2002 |
| WO | 02/087555 | 11/2002 |
| WO | 03/075958 | 9/2003 |
| WO | 2007/084670 | 7/2007 |
| WO | 2009/010290 A2 | 1/2009 |
| WO | 2010/072348 | 7/2010 |

(Continued)

OTHER PUBLICATIONS

Rudikoff et al. (Proceedings of the National Academy of Sciences USA, vol. 79, p. 1979-1983, 1982) (Year: 1982).*
Baxevanis (Expert Opinion: Drug Discovery, vol. 3, No. 4, p. 441-452, 2008) (Year: 2008).*
Ludwig et al. (Nature Reviews: Cancer, vol. 5, p. 845-856, 2005) (Year: 2005).*
Pepe et Al. (Journal of the National Cancer Institute, vol. 93, No. 14, p. 1054-1061, 2001) (Year: 2001).*
Mettlin et Al. (Cancer, vol. 74, No. 5, p. 1615-1620, 1994) (Year: 1994).*
Brawer et Al. (Urology, vol. 52, No. 3, p. 372-378, 1998) (Year: 1998).*
Budman et Al. (CUAJ, vol. 2, Issue 3, p. 212-221,2008) (Year: 2008).*

(Continued)

*Primary Examiner* — Michael Allen
(74) *Attorney, Agent, or Firm* — Grüneberg and Myers PLLC

(57) ABSTRACT

The instant invention provides for a new method of treating colorectal cancer (CRC) and metastases thereof in subjects, and preferably also of other solid cancers and metastases thereof in subjects, wherein said method preferably depends on whether the patient shows certain specific proteins levels in one or more body fluids prior to or during treatment, wherein said treatment comprises the administration of at least one pan αv integrin inhibitor to a patient, a medicament for use in said new methods, and a method of predicting the outcome of a treatment with at least one pan αv integrin inhibitor based on said specific protein levels in one or more body fluids of the patient.

6 Claims, 18 Drawing Sheets

Specification includes a Sequence Listing.

(56) References Cited

FOREIGN PATENT DOCUMENTS

| WO | 2010/096627 A1 | 8/2010 |
|---|---|---|
| WO | 2011/033006 | 3/2011 |
| WO | 2012/024612 A1 | 2/2012 |
| WO | WO 2012/107211 | 8/2012 |
| WO | 2012/167028 A2 | 12/2012 |
| WO | 2013/148288 | 10/2013 |
| WO | 2013/152313 A1 | 10/2013 |
| WO | 2014/135611 | 9/2014 |
| WO | 2016/041616 | 3/2016 |

OTHER PUBLICATIONS

Mantovani (European Journal of Cancer, vol. 30A, No. 3, p. 363-369, 1994) (Year: 1994).*
Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Johnson and Wu (Methods in Molecular Biology, Antibody Engineering: Methods and Protocols, vol. 248, p. 11-25, 2004) (Year: 2004).*
Aigner, K.R., Isolated liver perfusion. In: Morris DL, McArdle CS, Onik GM, eds. Hepatic Metastases. Oxford: Butterworth Heinemann, 1996, 101-107.
Altschul, et al., 1990, J. Mol. Biol.; 215:403-410.
Bates, RC et al., J Clin Invest 2005; 115: 339-47.
Bisanz, et al., Molecular Therapy 2005; 12, 634-643.
Coleman, RE, Oct. 2006, "Clinical features of metastatic bone disease and risk of skeletal morbidity". Clin. Cancer Res. 12 (20 Pt 2): 6243s-9s.
Desgrosellier, JS, et al., Nat Rev Cancer 2010; 10:9-22.
Elez, et al., 2014, Annals of Oncology 25:ii107-ii108.
Goodman, SL, et al., Biol Open 2012; 1:329-40.
Guise, TA, et al., Clin Cancer Res 2006; 12: 6213s-16s.
Guise, T, Oct. 2010, "Examining the metastatic niche: targeting the microenvironment", Semin. Oncol. 37 (Suppl 2): S2-14.
Jimenez-Andrade, JM, et al., Jun. 2010, "Bone cancer pain". Annals of the New York Academy of Sciences 1198: 173-81.
Legate, KR, et al. Nat Rev Mol Cell Biol 2006; 7:20-31.
McCabe, et al., Oncogene 2007; 26, 6238-6243.
Mitjans F, et al. J Cell Sci 1995; 108: 2825-38.
Monnier Y, et al. Cancer Res 2008: 68; 7323-31.
Zheng, et al. Cancer Research 1999; 59, 1655-1664.
Azare, et al., "Constitutively Activated Stat3 Induces Tumorigenesis and Enhances Cell Motility of Prostate Epithelial Cells through integren β6," Molecular and Cellular Biology; vol. 27, No. 12, pp. 4444-4453, Jun. 2007.
Garcia-Cordero et al., "A 1024-sample serum analyzer chip for cancer diagnostics," Lab Chip, 14, 2642-2650, 2014.
Kuku et al., "Serum Proinflammatory Mediators at Different Periods of Therapy in Patients With Multiple Myeloma," Mediators of inflamm. 2005:3 pp. 171-174, 2005. DOI:10.1155/MI.2005.171.
Liu et al. "Metastatic Signature in Lung Cancer is Associated with Sensitivity to Anti-Integrin $\alpha_v$ Monoclonal Antibody Intetumumab," Genes, Chromosomes & Cancer, 53:349-357, 2014.
Morgans et al., "Bone Targeted Agents: Preventing skeletal complications in prostate cancer," Urol Clin North Am 2012, 39(4), 533-546. DOI:10.1016/j.ucl.2012.07.009.
Munger et al. "Cross Talk among TGF-β Signaling Pathways, Integrins, and the Extracellular Matrix," Cold Spring Harbor Perspectives in Biol., 3:a005017, 17 pp., 2011.
Reardon et al., "Cilengitide: A Prototypic Integrin inhibitor for the Treatment of Glioblastoma and Other Malignancies," Genes and Cancer, 2(12) 1159-1165, 2011.
Wirth et al., "A Multicenter Phase 1 Study of EMD 525797 (DI17E6), a Novel Humanized Monoclonal Antibody Targeting αv integrins, in Progressive Castration-resistant Prostate Cancer with Bone Metatases After Chemotherapy," European Urology 65:897-904, 2014.
Amaral et al., Prostate Cancer; 2012, Article ID 327253.
Elez et al., WCGIC, Abstract No. O-0008; 2014, poster 65198, 1 page.
Elez et al., Annals of Oncology; 2014, 25 (suppl 4):iv167-iv209.
Heidenreich et al., Annals of Oncology; 2013, 24(2):329-336.
Jia et al., Anticancer Drugs; 2013, 24(3), 20 pages.
Miller et al., Annals of Oncology; 2014, 25 (Suppl 4), Abstract.
Pelosof et al., International Journal of Cancer; 2014, 134:596-605.
Trikha et al., Int J Cancer; 2004, 110(3), Abstract.
"International Nonproprietary Names for Phamaceutical Substances," WHO Drug Information, vol. 28, No. 1, 2014, Recommended INN: List 71, 52 pages.
Sequence Listing from U.S. Pat. No. 9,555,110 dated Jan. 31, 2017, 9 pages.
U.S. Appl. No. 16/518,174, filed Jul. 22, 2019, 2019/0338037, Straub et al.

* cited by examiner

METHOD OF TREATING SOLID CANCERS AND/OR METASTASES THEREOF WITH PAN AV INTEGRIN INHIBITOR, MEDICAMENTS THEREFORE, AND A METHOD OF PREDICTING THE CLINICAL OUTCOME OF TREATING SOLID CANCERS AND/OR METASTASES THEREOF

RELATED APPLICATIONS

This application is a U.S. national stage application of PCT international application PCT/EP2015/001699, filed on Aug. 18, 2015, which claims the benefit of U.S. provisional application SN: 62/051,530, filed on Sep. 17, 2014. The entire contents of the aforementioned applications are, hereby, incorporated by reference.

SEQUENCE LISTING

The instant application contains a Sequence Listing which has been submitted electronically in ASCII format and is, hereby, incorporated by reference in its entirety. Said ASCII copy, created on Mar. 15, 2017, is named P14170DOsequencelistingST25.txt and is 40,960 bytes in size.

BACKGROUND OF THE INVENTION

Field of the Invention

The instant invention provides for a new method of treating colorectal cancer (CRC) and metastases thereof in subjects, and preferably also of other solid cancers and metastases thereof in subjects, wherein said method preferably depends on whether the patient shows certain specific proteins levels in one or more body fluids prior to or during treatment, wherein said treatment comprises the administration of at least one pan αv integrin inhibitor to a patient, a medicament for use in said new methods, and a method of predicting the outcome of a treatment with at least one pan αv integrin inhibitor based on said specific protein levels in one or more body fluids of the patient.

More specifically, the instant invention provides for a new method of treating of solid cancers and/or metastases thereof, and especially of treating colorectal cancer (CRC) and/or metastases thereof, in subjects with at least one pan αv integrin inhibitor, preferably the pan αv integrin inhibitors abituzumab or intetumumab, wherein said subjects show certain specific protein levels in one or more body fluids prior to or during treatment.

Description of Related Art

Colorectal cancer (also known as colon cancer, rectal cancer or bowel cancer) is when cancer develops in the colon or rectum (parts of the large intestine). It is due to the abnormal growth of cells that have the ability to invade or spread to other parts of the body.

Treatments used for colorectal cancer may include some combination of surgery, radiation therapy, chemotherapy and targeted therapy. Cancers that are confined within the wall of the colon may be curable with surgery while cancer that has spread widely are usually not curable with management focusing on improving quality of life and symptoms. Five year survival rates in the United States are around 65%. This, however, depends on how advanced the cancer is, whether or not all the cancer can be removed with surgery, and the person's overall health. Globally, colorectal cancer is the third most common type of cancer making up about 10% of all cases. In 2012 it resulted in 1.4 million new cases and caused 694,000 deaths. It is more common in developed countries where more than 65% of occur. It is less common in women than men.

In both cancer of the colon and rectum, chemotherapy may be used in addition to surgery in certain cases. In rectal cancer, chemotherapy may be used in the neoadjuvant setting.

If cancer has entered the lymph nodes, adding the chemotherapy agents fluorouracil or capecitabine increases life expectancy. If the lymph nodes do not contain cancer, the benefits of chemotherapy are controversial. If the cancer is widely metastatic or unresectable, treatment is then palliative. Typically in this setting, a number of different chemotherapy medications may be used. Chemotherapy drugs for this condition may include capecitabine, fluorouracil, irinotecan, leucovorin, oxaliplatin and UFT. Another type of agent that is sometimes used are the epidermal growth factor receptor inhibitors.

While a combination of radiation and chemotherapy may be useful for rectal cancer, its use in colon cancer is not routine due to the sensitivity of the bowels to radiation. Just as for chemotherapy, radiotherapy can be used in the neo-adjuvant and adjuvant setting for some stages of rectal cancer.

Bone metastases, or metastatic bone disease, is a class of cancer metastases that results from primary tumor invasion to bone. Bone is one of the most common locations for metastasis. [Coleman R E (October 2006). "Clinical features of metastatic bone disease and risk of skeletal morbidity". Clin. Cancer Res. 12 (20 Pt 2): 6243s-9s.] While any type of cancer is capable of forming metastatic tumors within bone, the microenvironment of the marrow tends to favor particular types of cancer, including prostate, breast, and lung cancers. [Guise T (October 2010). "Examining the metastatic niche: targeting the microenvironment". Semin. Oncol. 37 (Suppl 2): S2-14.] Particularly in prostate cancer, bone metastases tend to be the only site of metastasis. [Jimenez-Andrade J M, Mantyh W G, Bloom A P, Ferng A S, Geffre C P, Mantyh P W (June 2010). "Bone cancer pain". Annals of the New York Academy of Sciences 1198: 173-81.]

One of the most common solid tumors is lung cancer, also known as carcinoma of the lung or pulmonary carcinoma, is a malignant lung tumor characterized by uncontrolled cell growth in tissues of the lung. If left untreated, this growth can spread beyond the lung by process of metastasis into nearby tissue or other parts of the body, including the liver, brain and bone. Most cancers that start in the lung, known as primary lung cancers, are carcinomas that derive from epithelial cells. The main primary types are small-cell lung carcinoma (SCLC), and non-small-cell lung carcinoma (NSCLC). Non-small-cell lung carcinoma (NSCLC) is any type of epithelial lung cancer other than small cell lung carcinoma (SCLC). As a class, NSCLCs and metastases thereof are relatively insensitive to chemotherapy, compared to small cell carcinoma. A wide variety of chemotherapies are used in metastatic NSCLC, unfortunately with little effect to date. Small-cell carcinoma or small-cell lung cancer (SCLC) is a type of highly malignant cancer that most commonly arises within the lung, although it can occasionally arise in other body sites, such as the cervix, prostate, and gastrointesinal tract. SCLC usually metastasizes widely very early on in the natural history of the tumor. Also in this case, the metastasis affects predominantely the bone, liver and brain.

The most common solid cancer in women is breast cancer. Breast cancer develops from breast tissue. It most commonly develops in cells from the lining of milk ducts and the lobules that supply the ducts with milk. Cancers developing from the ducts are known as ductal carcinomas, while those developing from lobules are known as lobular carcinomas. In addition, there are more than 18 other sub-types of breast cancer. The diagnosis of breast cancer is regularily confirmed by taking a biopsy of the concerning lump. Once the diagnosis is made, further tests are done to determine if the cancer has spread beyond the breast and which treatments it may respond to. If the cancer has spread beyond the breast, the breast cancer presents as metastatic disease. The symptoms caused by metastatic breast cancer will depend on the location of metastasis. Common sites of metastasis include bone, liver, lung and brain.

The metastatic process is a multistep event and represents the most dreadful aspect of cancer. At the moment of diagnosis, cancers are frequently far advanced in their natural history, and the presence of metastases is a common event. In fact, approximately 30% of patients have detectable metastases at the moment of clinical diagnosis and a further 30% of patients have occult metastases. Metastases can be disseminated and they can infest different organs at the same time, or localize to a specific organ. In the case of localized disease, surgery is the treatment of choice; however recurrence and prognosis depend on many criteria such as: resectability, patient's clinical situation, and number of metastases.

After resection, recurrence is common, suggesting that micrometastatic foci are present at the moment of diagnosis. Systemic chemotherapy is an ideal setting but only few patients are cured by it, and in the majority systemic chemotherapy fails. Many physiological barriers and pharmacokinetic parameters contribute to decrease its efficacy.

Liver, lungs and lymph nodes are filtration organs and therefore inclined to metastasization. The poor chemosensitivity of metastases, peculiarly those of colorectal origin has forced many researchers to use methods for increasing the time and the concentration of drugs. The need for decreasing or limiting the side effects for this important and delicate organ led to the development of the technique of liver isolation for perfusion of antineoplastic agents. (K. R. Aigner, Isolated liver perfusion. In: Morris D L, McArdle C S, Onik G M, eds. Hepatic Metastases. Oxford: Butterworth Heinemann, 1996. 101-107). Since 1981, modifications and technical improvements have been continuously introduced. Liver metastases may be of different origin and their chemosensitivity may vary according to the histological type and their response in presence of heat.

There still exists a growing need in the art in order to develop new therapeutic strategies for treating cancer, especially metastases, systemically.

SUMMARY OF THE INVENTION

The object of the present invention therefore was to develop such a new strategy. It should be applicable to systemic treatment, and it should lower the dose and/or increase the efficiency of the cancer therapeutical agents to be applied. A further object was to normalize tumor vasculature to increase delivery of systemic therapeutics of tumor, i.e. to reset the tumor vasculature to the functionality of the vasculature of non-tumor tissue.

Thus, it is a preferred objective of the instant invention to provide a more effective, better tolerated treatment for humans, especially human cancer patients suffering from solid cancers and/or metastases thereof, preferably colorectal cancer (CRC) and/or metastases thereof and especially metastatic colorectal cancer (mCRC), preferably independent from the location of the metastases, thus preferably leading to enhanced overal survival (OS), progression-free survival (PFS), quality of life (QOL) and/or increased median survival.

DETAILED DESCRIPTION OF THE INVENTION

Figure 1:
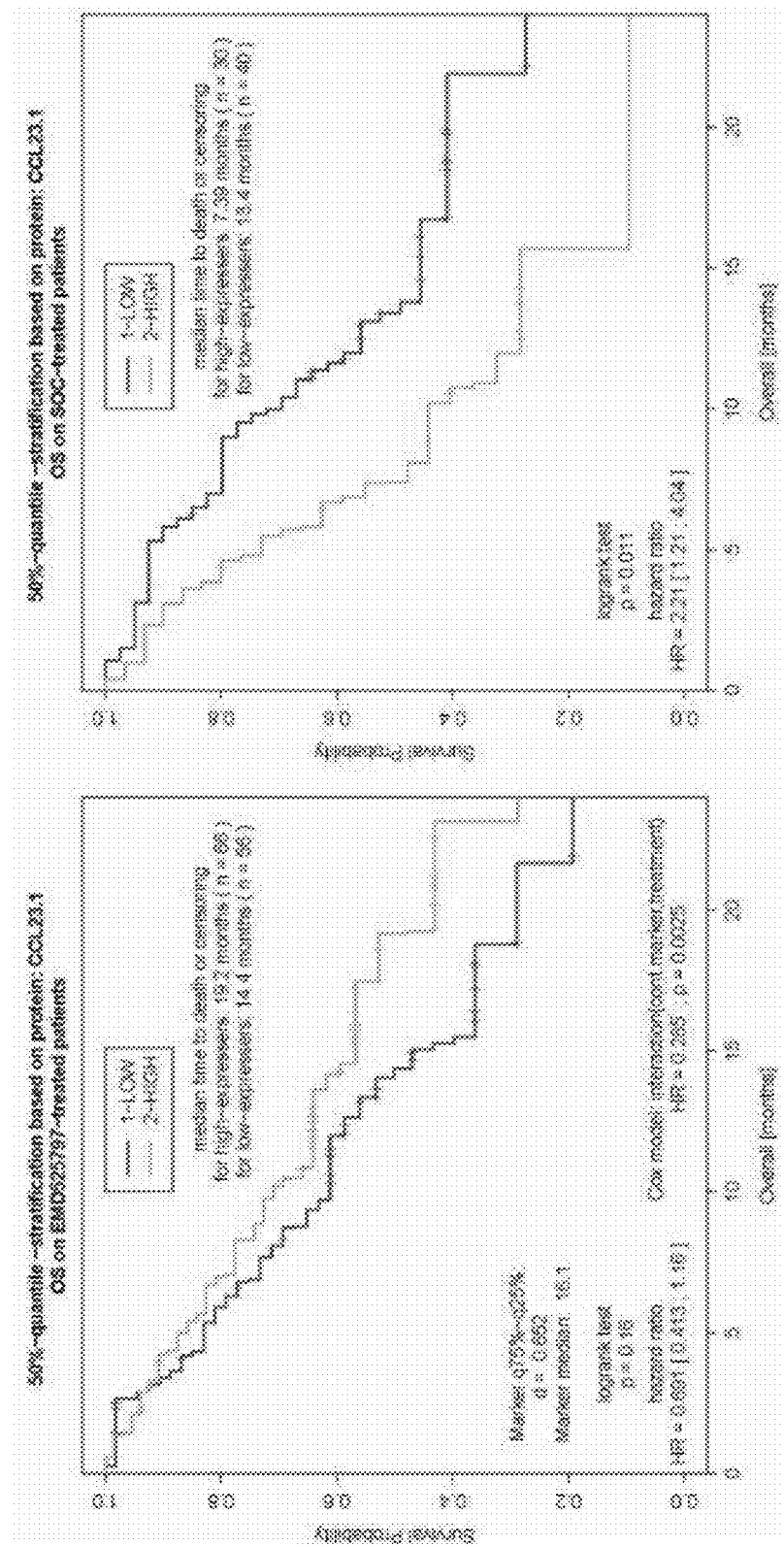
FIG. 1 shows a graph of the 50%-quantile stratification, based on protein CCL23.1, of overall survival on EMD525797-treated patients and on SOC-treated patients.

Prostate cancer is the most commonly occurring solid cancer aside skin cancer in the US, and is the second most common cause of male cancer deaths.

Prostate cancer is classified in four stages: Stage I prostate cancer is found in the prostate only and cannot be felt during a digital rectal exam nor is it visible by imaging. In stage II prostate cancer, the tumor has grown inside the prostate but has not extended beyond it, whereas in stage III, the cancer has spread outside the prostate, but to a minimal extent only. Often, prostate cancer in stage III will have spread only to nearby tissues, such as the seminal vesicles. Finally, in stage IV, the cancer has spread outside the prostate to other tissues, such as the lymph nodes, bones, liver, and/or lungs or brain.

The spectrum of prostate cancers that are progressing despite castrate levels of testosterone includes tumors that have shown varying degrees and durations of response to primary hormone treatment, and clinical manifestations that range from a rising prostate-specific antigen (PSA) alone, a rising PSA with osseous and/or soft-tissue spread, or a predominantly visceral disease pattern.

Currently approved treatment of prostrate cancer includes surgical castration, chemical castration, or a combination of surgical and chemical castration. Removal of the testes, the primary testosterone producing organ, reduces the levels of circulating androgens, to less than 5% of normal levels. This reduction in androgen levels inhibits prostate tumor growth. Although the anti-tumor effects of surgical castration are direct, the anti-tumor effects can be temporary. Surgical castration often leads to clonal selection of androgen-independent prostate tumor cells. This results in re-growth of the prostate tumor in a form that proliferates without testosterone or DHT Stimulation. Chemical castration (also called medical castration) is often substituted for surgical castration, as an initial treatment. Despite its high prevalence, treatment options for men having prostate cancer remain relatively limited and typically depend on the stage of the cancer.

Treatment options include surgical treatments such as radical prostatectomy, in which the prostate is completely removed and radiation, applied through an external beam that directs the dose to the prostate from outside the body or via low-dose radioactive seeds that are implanted within the prostate to kill cancer cells locally. Anti-androgen hormone therapy also is used in the treatment of prostate cancer, either alone or in conjunction with surgery or radiation. Hormone therapy typically aims at blocking the pituitary from producing hormones that stimulate testosterone production by use of castration or administration of hormone analogs and requires that patients have injections of these hormone analogs for protracted periods. Finally, chemotherapeutic approaches have been used to treat advanced prostate cancer, usually as a last resort when other approaches have failed. Since a couple of years, the combination of docetaxel and prednisone was established as the new standard of care for patients who have progressed on androgen deprivation.

None of the treatments described above are curative and prostate cancer being androgen dependent at first, often will progress despite surgical and hormonal-based therapies, and become resistant over time, leading to a cancer type which is called "hormone refractory cancer" or "castration resistant cancer" (CRPC).

Clinical disease manifestations of CRPC are commonly related to bone metastases and may include pain, pathologic fractures, and spinal cord compression, with local recurrences that may be associated with pelvic discomfort, renal dysfunction due to ureteral compression, bladder outlet obstruction, and sexual dysfunction. Further, while bone cancer is the predominant result of CRPC, patients may develop soft-tissue metastases (lymph node(s)) and visceral metastasis in liver, lung, brain, and other organs. Patients with CRPC are minimally responsive to chemotherapy and the majority of patients die due to progressive prostate cancer within 20 months of initiating treatment. Bisphosphonates are commonly used in patients with castrate-resistant prostate cancer who have bone metastases.

It has been shown that prostate tumors remain dormant and clinically undetectable until they begin to secrete angiogenic factors and down-regulate the expression of angiogenic inhibitors. In general, it can be stated that angiogenesis is critical to the genesis of prostate tumors. Therefore, it was not completely surprising that anti-angiogenic agents may inhibit prostate cancer cell growth.

In prostate cancer, tumor cells express an abnormal integrin repertoire and are surrounded by a markedly aberrant extracellular matrix (ECM). These changes have profound consequences, given the ability of each integrin to regulate specific cell functions. Expression of $\beta 3$ and $\beta 1$ subunits activates specific signaling pathways and support distinct cancer cell functions. $\beta 3$ is uniquely required in cancer cells for increasing cdc2 levels as well as cdc2 kinase activity. These effects are specific for $\beta 3$ and are not observed for $\beta 6$. Up-regulation of $\beta 3$ and $\beta 6$ integrin variants has been described. Zheng et al. (Cancer Research 1999; 59, 1655-1664) used human prostate cancer cells isolated from sixteen surgical specimens, to show that these cells express $\alpha v \beta 3$, whereas normal prostate epithelial cells do not. Similarly, $\alpha v \beta 6$ was found to be expressed in adenocarcinoma (Li et al.; Molecular and Cellular Biology 2007; 27, 4444).

The use of integrin inhibitors is likely to affect both cancer cell survival and angiogenesis since integrins are expressed by tumor cells as well as by endothelial cells. Although it is hard to discriminate between an effect on tumor growth and an effect on angiogenesis, a maximal response of these inhibitors can be predicted when the targeted integrin is expressed by both tumor and endothelial cells.

Bone is the most frequent metastatic site for prostate cancer. Bisanz et al. (Molecular Therapy 2005; 12, 634-643) illustrate a positive role for alpha-v integrins on prostate tumor survival in the bone. Analysis of human prostate cancer bone xenografts shows that intratumoral administration of liposome encapsulated human alpha-v siRNAs significantly inhibits the growth of PC3 tumors in bone and increases apoptosis of prostate tumor cells. Further studies (McCabe et al., Oncogene 2007; 26, 6238-6243) demonstrate that $\alpha v \beta 3$ integrin activation on tumor cells is essential for the recognition of key bone specific matrix proteins. These data suggest that the $\alpha v \beta 3$ integrin modulates prostate cancer growth in distant metastasis. Since integrins mediate the interactions between tumor cells and bone microenvironment and facilitate growth in bone, a potential application of the use of integrin inhibitors is to prevent prostate cancer bone lesions. These lesions are osteoblastic and/or osteolytic and are frequently detected in prostate cancer patients (over 80% of prostate cancer patients have established bone metastasis at autopsy).

A recent study has shown that the αvβ3 integrin promotes bone gain mediated by prostate cancer cells that metastasize to the bone and point to αvβ3 as a potential therapeutic target to block prostate cancer osteoblastic lesions. Immunohistochemical analysis has demonstrated the presence of αv integrin in a large proportion of human prostate cancer tissues samples.

These and other results suggest that anti-integrin agents may have both direct and indirect antitumor activity. But there are only few clinical trials reporting that peptide or non-peptide integrin inhibitors are effective agents in prostate cancer therapy.

Therefore, there is also a need to provide a method of treatment of bone metastases, preferably bone metastases of breast cancer, lung cancer and/or prostate cancer. Moreover, there is a especially high need to provide a method for the treatment of prostate cancer bone metatases, especially castration-resistant prostate cancer bone metastases.

Therefore, there is a also a need to provide a method of treatment of bone metastases from metastatic androgen independent prostate cancer (mAIPCa) and/or bone metastases from metastatic androgen dependent prostate cancer (mADPCa).

According to an aspect of the invention there is provided a method for identifying solid cancer and/or metastases in a subject, preferably a human subject, that are susceptible to treatment with at least one pan αv integrin inhibitor, preferably Abituzumab or Intetumumab, comprising determining said certain proteins levels in one or more body fluids, whereby a high level of one or more proteins selected from a first group of said specific proteins and/or a low level of one or more proteins from a second group of said specific proteins indicates the tumor is susceptible to said treatment.

Thus, preferred subject of the invention is a method of treating solid cancers and/or metastases thereof in a subject, wherein said subject is characterised by a) high levels of one or more proteins in at least one body fluid of said subject, wherein said one or more proteins are selected from the group consisting of:
TPO (UniProt ID: P07202),
CCL23.1 (UniProt ID: P55773),
IGHD_IGK._IGL. (UniProt ID: P01880),
TK1 (UniProt ID: P04183),
IL17A (UniProt ID: Q16552),
STX1A (UniProt ID: Q16623), and
PGF (UniProt ID: P49763),
and/or b) low levels of one protein in at last one body fluid of said subject, wherein said protein is:
TG M3 (UniProt ID: Q08188);

said method comprising administering to said subject at least one pan αv integrin inhibitor. Preferably, said at least one pan αv integrin inhibitor comprises, or is, Abituzumab and/or Intetumumab. More preferably, said at least one pan αv integrin inhibitor is Abituzumab and/or Intetumumab, especially preferably Abituzumab.

Preferred ia said method, wherein the level of said protein in at least one body fluid of said subject is a) classified as high, if the respective protein level in said blood plasma is at least 2% higher, more preferably at least 5% higher, even more preferably at least 10% higher and especially at least 25% higher than the median threshold determined for the respective protein, and/or b) classified as low, if the respective protein level in said blood plasma is at least 2% lower, more preferably at least 5% lower, even more preferably at least 10% lower and especially at least 25% lower than said median threshold for the respective protein.

Preferred ia said method, wherein said threshold or median threshold for the respective protein is determined from the body fluid of a plurality of subjects being part of a diseased subject population suffering from the said solid cancer, preferably said colorectal cancer (CRC) and/or metastases thereof, and especially metastatic colorectal cancer (mCRC).

Body fluids are preferably the liquids originating from inside the bodies of living subjects, preferably living human subjects. They include fluids that are excreted or secreted from the body as well as body water that normally is not excreted or secreted.

The body fluids can preferably specified by type, such as intracellular fluids, extracellular fluids, intravascular fluids (e.g. whole blood, blood and blood plasma), interstitial fluids, lymphatic fluids (sometimes regarded as a subtype of interstitial fluids), and transcellular fluids.

Preferred body fluids are selected from the group consisting of whole blood (preferably also referred to as "blood"), blood serum (preferably also referred to as "serum"), blood plasma (preferably also referred to as "plasma"), exudate, lymph, mucus, peritoneal fluid, saliva, sputum, tears and urine. Especially preferred body fluids are selected from the group consisting of Preferred body fluids are selected from the group consisting of whole blood (preferably also referred to as "blood"), blood serum (preferably also referred to as "serum"), and blood plasma (preferably also referred to as "plasma"). Especially preferred is blood plasma (preferably also referred to as "plasma"). Alternatively preferred is blood serum (preferably also referred to as "serum"), and whole blood (preferably also referred to as "blood").

The threshold for categorization of patients into "low level" or "high level" for each of said specific proteins is preferably determined by listing of all avaiblable levels for that respective specific protein in the respective body fluid, then determining the median from this listing of said specific protein level values in said body fluid, and taking this median value as the threshold.

This threshold is preferably also referred to herein as median threshold. Preferably, said threshold or median threshold is determined in the population of subjects suffering from the respective bone metastasis disease as described herein. More preferably, said threshold or median threshold for the respective specific protein is determined from the body fluid of a plurality of subjects being part of a diseased subject population suffering from the respective bone metastasis disease.

More preferably, said threshold or median threshold is determined in the population of subjects suffering from the respective solid cancer as described herein, especially in the population of subjects suffering from colorectal cancer (CRC) and/or metastases thereof. Even more preferably, said threshold or median threshold for the respective specific protein is determined from the body fluid of a plurality of subjects being part of a diseased subject population suffering from the respective bone respective solid cancer as described herein. Even more preferably, said threshold or median threshold for the respective specific protein is determined from the body fluid of a plurality of subjects being part of a diseased subject population suffering from the from colorectal cancer (CRC) and/or metastases thereof. Especially preferably, said threshold or median threshold for the respective specific protein is determined from the body fluid of a plurality of subjects being part of a diseased subject population suffering from the from metastatic colorectal cancer (mCRC).

For example, for determining said median threshold for one or more said specific proteins, body fluid samples (here: blood samples) are taken from 197 human subjects suffering from metastatic colorectal cancer (mCRC) in order to obtain about 500 μL offer a preferred body fluid (here: blood plasma). The levels of the contained specific proteins of interest, e.g. STX1A, are determined using an aptamer based protein detection system, e.g. the SomaLogic Proteomic Affinity Assay Method described in detail in the Experimental Section, whereby results for each protein of interest are represented by relative fluorescence readouts reported by the detection system. In an optional next step, the obtained raw data set can be simplified by removing the data of proteins not of interest, e.g. proteins that are known to be derived or affected by inadequate sample handling during plasma protein, such as platelet activation or cell lysis which may occur during the plasma preparation process. The thus obtained (optionally simplified) day that said is then preferably subjected to steps such as Data normalization and filtering procedures in order to obtain robust signals of the proteins of interest. Preferably, this data analysis process includes a cut-of optimisation. This procedure thus provides a median threshold of one or more specific proteins of interest, e.g. the median threshold for the protein STX1A. Taking this obtained median threshold, both said 197 human subjects suffering from metastatic colorectal cancer (mCRC), as well as future human subjects suffering from mCRC, can then be readily characterised as having a high level or a low level, respectively, of one or more specific proteins of interest, e.g. STX1A, with the predicted specific impact on the clinical outcome of the treatment with at least one pan αv integrin inhibitor, optionally in combination with one or more chemotherapeutic agents.

Preferably, the body fluid sampling and/or the evaluation of the median value for the respective specific protein is performed prior to treatment of the respective solid cancer, colorectal cancer and/or metastases therof, or other bone metastasis disease, preferably colorectal cancer and/or metastases thereof, and especially metastatic colorectal cancer (mCRC), with said at least one pan αv integrin inhibitor. Preferably, patients are classified as "high level" if their respective specific protein level in said body fluid is higher than the median threshold. Accordingly, patients are preferably classified as "low level" if their respective specific protein level in said body fluid is lower than or equal to said median threshold.

More preferably, the threshold for categorization of patients into "low level" or "high level" for each of said specific proteins is preferably determined by listing of all avaiblable levels for that respective specific protein in the blood plasma, then determining the median from this listing of said specific protein level values in said blood plasma, and taking this median value as the threshold. This threshold is preferably also referred to herein as median threshold. Preferably, the blood plasma sampling and/or the evaluation of the median value for the respective specific protein is performed prior to treatment of the respective solid cancer, colorectal cancer and/or metastases therof, or other bone metastasis disease, preferably colorectal cancer and/or metastases thereof, and especially metastatic colorectal cancer (mCRC), with said at least one pan αv integrin inhibitor. Preferably, patients are classified as "high level" if their respective specific protein level in said blood plasma is higher than the median threshold. Accordingly, patients are preferably classified as "low level" if their respective specific protein level in said blood plasma is lower than or equal to said median threshold. Preferably, the solid cancer and/or metastases thereof in this regard is colorectal cancer and/or metastases thereof and especially metastatic colorectal cancer (mCRC). Preferably, the at least one pan αv integrin inhibitor comprises Abituzumab or Intetumumab). More preferably, the at least one pan αv integrin inhibitor is Abituzumab or Intetumumab. especially preferred, the at least one pan αv integrin inhibitor is Abituzumab.

More preferably, the threshold for categorization of patients into "low level" or "high level" for each of said specific proteins is preferably determined by listing of all avaiblable levels for that respective specific protein in the blood plasma, then determining the median from this listing of said specific protein level values in said blood plasma, and taking this median value as the threshold. This threshold is preferably also referred to herein as median threshold. Preferably, the blood plasma sampling and/or the evaluation of the median value for the respective specific protein is performed prior to treatment of the respective solid cancer, colorectal cancer and/or metastases therof, or other bone metastasis disease, preferably colorectal cancer and/or metastases thereof, and especially metastatic colorectal cancer (mCRC), with said at least one pan αv integrin inhibitor. Preferably, patients are classified as "high level" if their respective specific protein level in said blood plasma is higher than the median threshold. Accordingly, patients are preferably classified as "low level" if their respective specific protein level in said blood plasma is lower than or equal to said median threshold. Preferably, the solid cancer and/or metastases thereof in this regard is colorectal cancer and/or metastases thereof and especially metastatic colorectal cancer (mCRC). Preferably, the at least one pan αv integrin inhibitor comprises Abituzumab or Intetumumab). More preferably, the at least one pan αv integrin inhibitor is Abituzumab or Intetumumab. especially preferred, the at least one pan αv integrin inhibitor is Abituzumab.

Methods to determine said threshold level and especially said median threshold level are known in the art. Examples of suitable technologies include, but are not limited to the SomaLogic technology, preferably the SomaLogic Proteomic Affinity Assay technology, SomaLogic SOMAscan™/V3/Version 10.5.1.1, ELISA (Enzyme-Linked Immuno-Sorbent Assays) technologies and variants therof, including the RIA (Radio Immuno Assay) technology as high sensitivity variant, the 2D SDS-Polyacryamid electrophorese (SDS-PAGE) Mass Spectrometry technology, and Proximity Ligation Assay (PLA) technologies.

More specifically, the threshold for classification of patients into the 'high' and 'low' groups on the basis of plasma levels of the mentioned proteins is preferably the median plasma level across the patient population. The threshold may show a slight, but irrelevant dependency from the actual technology employed.

Preferably, protein plasma levels of samples that are to be classified are measured using the SomaLogic technology, preferably the SomaLogic Proteomic Affinity Assay technology (Somalogic, Inc., 2945 Wilderness Pl, Boulder, Colo. 80301, USA, software package and version number as described herein) as described herein. The median plasma levels that are accordingly identified can be used as threshold for classification into 'low' and 'high' categories, preferably after the new SomaLogic patient profile is processed with data normalization steps, such as it has been performed in the analysis described herein. For example, the patient's pre-treatment proteomic profiles on 888 plasma protein levels—as it is prepared by the SomaLogic system—can advantageously be combined with existing pre-treatment data set for all samples, variance stabilzation as implemented in the vsn2 package which was applied. Finally, the normalized patient's pre-treatment level for the specific protein of intererest can be retrieved and compared with the specific median threshold for the protein of interest (median thresholds for predicitivity for OS-CCL23: 16.1 signal units, IGHD_IGK_IGL: 11.3, TPO: 11.2, IL17A: 7.64, TGM3: 8.19, TK1: 9.53, STX1A: 8.96, median thresholds for predicitivity for PFS-PGF: 8.62; all median thresholds are given as protein level units on a log2 scale as measured by Somalogic technology and after variance-stabilizing normalization of the data set) as received from the clinical study described herein (POSEIDON study). In case no prior data set is available, or the technology to measure the plasma protein levels is not the SomaLogic technology, the median population plasma level—as it comes from the new technology or the new patient population (that preferably comprises at least 120 patients for the respective indication)is preferably termed first, then classification can be readily done on the basis of the new population median.

Especially preferably, patients are classified as "high level" if their respective specific protein level in said blood plasma is at least 2% higher, more preferably at least 5% higher, even more preferably at least 10% higher and especially at least 25% higher than said median threshold for the respective specific protein.

Especially preferably, patients are classified as "low level" if their respective specific protein level in said blood plasma is at least 2% lower, more preferably at least 5% lower, even more preferably at least 10% lower and especially at least 25% lower than said median threshold for the respective specific protein.

Usually, said thresholds and/or said median thresholds are determined in a subject population having a solid tumor and/or metastases thereof, preferably the respective solid tumor and/or metastases thereof.

Preferably, this is done independently for each respective specific protein of interrest.

More preferably, said threshold and/or said median threshold is determined in a subject population having colorectal cancer and/or metastases thereof, preferably independently for each respective specific protein of interrest.

Preferably, said specific proteins according to the invention comprise a) one or more proteins, selected from the group consisting of TPO (Somamer ID: SL000588; UniProt ID: P07202),
CCL23.1 (Somamer ID: SL003302; UniProt ID: P55773),
IGHD_IGK._IGL. (Somamer ID: SL000460; UniProt ID: P01880),
TK1 (Somamer ID: SL000057; UniProt ID: P04183),
IL17A (Somamer ID: SL001713; UniProt ID: Q16552),
STX1A (Somamer ID: SL004304; UniProt ID: Q16623), and
PGF (Somamer ID: SL002640; UniProt ID: P49763), and/or b) one protein, selected which is
TG_M3 (Somamer ID: SL008945; UniProt ID: Q08188);
and/or preferably also proteins having at least 80%, more preferably at least 90%, even more preferably at least 95% and especially at least 99% sequence homology to said specific proteins.

More preferably, a high level as defined herein for one or more specific proteins in the respective body fluid, preferably in the blood plasma, of the patient is advantageous with respect to the clinical outcome, if said high level of said one or more specific proteins in said body fluid comprises one or more of the proteins selected from the group consisting of TPO (Somamer ID: SL000588; UniProt ID: P07202),
CCL23.1 (Somamer ID: SL003302; UniProt ID: P55773),
IGHD_IGK._IGL. (Somamer ID: SL000460; UniProt ID: P01880),
TK1 (Somamer ID: SL000057; UniProt ID: P04183),
IL17A (Somamer ID: SL001713; UniProt ID: Q16552),
STX1A (Somamer ID: SL004304; UniProt ID: Q16623), and
PGF (Somamer ID: SL002640; UniProt ID: P49763), and/or preferably also proteins having at least 80%, more preferably at least 90%, even more preferably at least 95% and especially at least 99% sequence homology to said specific proteins.

More preferably, a low level as defined herein for one or more specific proteins in the respective body fluid, preferably in the blood plasma, of the patient is advantageous with respect to the clinical outcome of the treatment of the respective solid cancer, colorectal cancer and/or metastases therof, or other bone metastasis disease, preferably colorectal cancer and/or metastases thereof, and especially metastatic colorectal cancer (mCRC), with the at least one pan αv integrin inhibitor, if said low level of said one or more specific proteins in said body fluid comprises the protein TGM3 (Somamer ID: SL008945; UniProt ID: Q08188);
and/or preferably also a protein having at least 80%, more preferably at least 90%, even more preferably at least 95% and especially at least 99% sequence homology to said specific protein.

Especially prefered is a method as described herein, wherein said subject is characterised by a high level of the protein STX1A (UniProt ID: Q16623)
and/or a protein having at least 80%, more preferably at least 90% even more preferably 95% and especially at least 99% sequence homology to said protein.

Preferably, sequence homology of the proteins described herein is determined using BLASTp algorithms.

Said specific proteins are preferably characterised by the following sequences and /or sequence IDs (Amino acid sequences of protein listed in Table 1 as identified by UniProt IDs in FASTA format):

Amino acid sequences of protein mentioned in table 1 as identified by UniProt IDs in FASTA format:

TPO (Thyroid peroxidase) (SEQ ID NO: 10):

```
>sp|P07202|PERT_HUMAN Thyroid peroxidase
OS = Homo sapiens GN = TPO PE = 1 SV = 4
MRALAVLSVTLVMACTEAFFPFISRGKELLWGKPEESRVSSVLEESKR

LVDTAMYATMQRNLKKRGILSPAQLLSFSKLPEPTSGVIARAAEIMET

SIQAMKRKVNLKTQQSQHPTDALSEDLLSIIANMSGCLPYMLPPKCPN

TCLANKYRPITGACNNRDHPRWGASNTALARWLPPVYEDGFSQPRGWN

PGFLYNGFPLPPVREVTRHVIQVSNEVVTDDDRYSDLLMAWGQYIDHD

IAFTPQSTSKAAFGGGADCQMTCENQNPCFPIQLPEEARPAAGTACLP

FYRSSAACGTGDQGALFGNLSTANPRQQMNGLTSFLDASTVYGSSPAL

ERQLRNWTSAEGLLRVHARLRDSGRAYLPFVPPRAPAACAPEPGIPGE

TRGPCFLAGDGRASEVPSLTALHTLWLREHNRLAAALKALNAHWSADA

VYQEARKVVGALHQIITLRDYIPRILGPEAFQQYVGPYEGYDSTANPT
```

VSNVFSTAAFRFGHATIHPLVRRLDASFQEHPDLPGLWLHQAFFSPWT

LLRGGGLDPLIRGLLARPAKLQVQDQLMNEELTERLFVLSNSSTLDLA

SINLQRGRDHGLPGYNEWREFCGLPRLETPADLSTAIASRSVADKILD

LYKHPDNIDVWLGGLAENFLPRARTGPLFACLIGKQMKALRDGDWFWW

ENSHVFTDAQRRELEKHSLSRVICDNTGLTRVPMDAFQVGKFPEDFES

CDSITGMNLEAWRETFPQDDKCGFPESVENGDFVHCEESGRRVLVYSC

RHGYELQGREQLTCTQEGWDFQPPLCKDVNECADGAHPPCHASARCRN

TKGGFQCLCADPYELGDDGRTCVDSGRLPRVTWISMSLAALLIGGFAG

LTSTVICRWTRTGTKSTLPISETGGGTPELRCGKHQAVGTSPQRAAAQ

DSEQESAGMEGRDTHRLPRAL

CCL23.1 (Chemokine (C-C motif) ligand 23) (SEQ ID NO: 11):

>sp|P55773|CCL23_HUMAN C-C motif chemokine 23
OS = Homo sapiens GN = CCL23 PE = 1 SV = 3
MKVSVAALSCLMLVTALGSQARVTKDAETEFMMSKLPLENPVLLDRFH

ATSADCCISYTPRSIPCSLLESYFETNSECSKPGVIFLTKKGRRFCAN

PSDKQVQVCVRMLKLDTRIKTRKN

IGHD_IGK._IGL. (Immuno-globulin D) (SEQ ID NO: 12):

>sp|P018801|IGHD_HUMAN Ig delta chain C region
OS = Homo sapiens GN = IGHD PE = 1 SV = 2
APTKAPDVFPIISGCRHPKDNSPVVLACLITGYHPTSVTVTWYMGTQS

QPQRTFPEIQRRDSYYMTSSQLSTPLQQWRQGEYKCVVQHTASKSKKE

IFRWPESPKAQASSVPTAQPQAEGSLAKATTAPATTRNTGRGGEEKKK

EKEKEEQEERETKTPECPSHTQPLGVYLLTPAVQDLWLRDKATFTCFV

VGSDLKDAHLTWEVAGKVPTGGVEEGLLERHSNGSQSQHSRLTLPRSL

WNAGTSVTCTLNHPSLPPQRLMALREPAAQAPVKLSLNLLASSDPPEA

ASWLLCEVSGFSPPNILLMWLEDQREVNTSGFAPARPPPQPGSTTFWA

WSVLRVPAPPSPQPATYTCVVSHEDSRTLLNASRSLEVSYVTDHGPMK

TGM3 (Protein-glutamine gamma-glutamyl-transferase E) (SEQ ID NO: 13):

>sp|Q08188|TGM3_HUMAN Protein-glutamine gamma-glutamyltransferase E OS = Homo sapiens
GN = TGM3 PE = 1 SV = 4
MAALGVQSINWQTAFNRQAHHTDKFSSQELILRRGQNFQVLMIMNKGL

GSNERLEFIVSTGPYPSESAMTKAVFPLSNGSSGGWSAVLQASNGNTL

TISISSPASAPIGRYTMALQIFSQGGISSVKLGTFILLFNPWLNVDSV

FMGNHAEREEYVQEDAGIIFVGSTNRIGMIGWNFGQFEEDILSICLSI

LDRSLNFRRDAATDVASRNDPKYVGRVLSAMINSNDDNGVLAGNWSGT

YTGGRDPRSWNGSVEILKNWKKSGFSPVRYGQCWVFAGTLNTALRSLG

IPSRVITNFNSAHDTDRNLSVDVYYDPMGNPLDKGSDSVWNFHVWNEG

WFVRSDLGPSYGGWQVLDATPQERSQGVFQCGPASVIGVREGDVQLNF

DMPFIFAEVNADRITWLYDNTTGKQWKNSVNSHTIGRYISTKAVGSNA

RMDVTDKYKYPEGSDQERQVFQKALGKLKPNTPFAATSSMGLETEEQE

PSIIGKLKVAGMLAVGKEVNLVLLLKNLSRDTKTVTVNMTAWTIIYNG

TLVHEVWKDSATMSLDPEEEAEHPIKISYAQYEKYLKSDNMIRITAVC

KVPDESEVVVERDIILDNPTLTLEVLNEARVRKPVNVQMLFSNPLDEP

VRDCVLMVEGSGLLLGNLKIDVPTLGPKEGSRVRFDILPSRSGTKQLL

ADFSCNKFPAIKAMLSIDVAE

STX1A (Syntaxin 1α) (SEQ ID NO: 14):

>sp|Q16623|STX1A_HUMAN Syntaxin-1A OS = Homo sapiens GN = STX1A PE = 1 SV = 1
MKDRTQELRTAKDSDDDDDVAVTVDRDRFMDEFFEQVEEIRGFIDKIA

ENVEEVKRKHSAILASPNPDEKTKEELEELMSDIKKTANKVRSKLKSI

EQSIEQEEGLNRSSADLRIRKTQHSTLSRKFVEVMSEYNATQSDYRER

CKGRIQRQLEITGRTTTSEELEDMLESGNPAIFASGIIMDSSISKQAL

SEIETRHSEIIKLENSIRELHDMFMDMAMLVESQGEMIDRIEYNVEHA

VDYVERAVSDTKKAVKYQSKARRKKIMIIICCVILGIVIASTVGGIFA

TK1 (Thymidine kinase 1) (SEQ ID NO: 15):

>sp|P04183|KITH_HUMAN Thymidine kinase, cytosolic OS = Homo sapiens GN = TK1 PE = 1
SV = 2
MSCINLPTVLPGSPSKTRGQIQVILGPMFSGKSTELMRRVRRFQIAQY

KCLVIKYAKDTRYSSSFCTHDRNTMEALPACLLRDVAQEALGVAVIGI

DEGQFFPDIVEFCEAMANAGKTVIVAALDGTFQRKPFGAILNLVPLAE

SVVKLTAVCMECFREAAYTKRLGTEKEVEVIGGADKYHSVCRLCYFKK

ASGQPAGPDNKENCPVPGKPGEAVAARKLFAPQQILQCSPAN

IL17A (Interleukin-17A) (SEQ ID NO: 16):

>sp|Q16552|IL17_HUMAN Interleukin-17A OS = Homo sapiens GN = IL17A PE = 1 SV = 1
MTPGKTSLVSLLLLLSLEAIVKAGITIPRNPGCPNSEDKNFPRTVMVN

LNIHNRNTNTNPKRSSDYYNRSTSPWNLHRNEDPERYPSVIWEAKCRH

LGCINADGNVDYHMNSVPIQQEILVLRREPPHCPNSFRLEKILVSVGC

TCVTPIVHHVA

PGF (Placental growth factor) (SEQ ID NO: 17):

>sp|P49763|PLGF_HUMAN Placenta growth factor
OS = Homo sapiens GN = PGF PE = 1 SV = 2
MPVMRLFPCFLQLLAGLALPAVPPQQWALSAGNGSSEVEVVPFQEVWG

RSYCRALERLVDVVSEYPSEVEHMFSPSCVSLLRCTGCCGDENLHCVP

VETANVTMQLLKIRSGDRPSYVELTFSQHVRCECRHSPGRQSPDMPGD

FRADAPSFLPPRRSLPMLFRMEWGCALTGSQSAVWPSSPVPEEIPRMH

PGRNGKKQQRKPLREKMKPERCGDAVPRR

Specific proteins according to the invention are preferably also proteins having at least 80%, more preferably at least 90%, even more preferably at least 95% and especially at least 99% sequence homology to the afore described sequences.

As further described herein, a high level of one or more proteins of a first group of said specific proteins and/or a low level of one or more proteins from a second group of specific proteins is predictive for improved clinical benefit, preferably clinical benefit as described herein, under treatment with at least one pan αv integrin inhibitor, preferably including or consisting of Abituzumab, for subjects suffering from colorectal cancer (CRC) and/or metastases thereof and especially for subjects suffering from metastatic colorectal cancer (mCRC). Preferably, a high level of one or more proteins of a first group of said specific proteins and/or a low level of one or more proteins from a second group of specific proteins is predictive for improved overall survival and/or improved progression free survival, under treatment with at least one pan αv integrin inhibitor, preferably including or consisting of Abituzumab, for subjects suffering from solid cancers and/or metastases thereof.

In an alternatively preferred embodiment, Intetumumab (CNTO-95) can be employed as the at least one pan αv integrin inhibitor in the method according to the invention, instead of Abituzumab.

Said protein levels for said specific proteins are preferably at the same time negative prognostic indicating that the biologically addressed by the markers plays a role both for disease prognosis (summarized in Table 2).

TABLE 1

Clinical outcome dependent on the respective specific protein level under Abituzumab treatment:

| Gene symbol (Somamer ID) | UniProt ID | Patients with benefit have High(er) or Low(er) plasma levels compared to median | Survival endpoint for which benefit is observed | Hazard Ratio (HR) of overall survival (OS) * [CI 95%] *except PGF | Logrank test p-value |
|---|---|---|---|---|---|
| TPO Thyroid peroxidase (SL000588) | P07202 | High | OS | 0.472 [0.260-0.855] | 0.015 |
| CCL23.1 Chemokine (C-C motif) ligand 23 (SL003302) | P55773 | High | OS | 0.400 [0.227-0.706] | 0.0022 |
| IGHD_IGK._IGL. Immuno-globulin D (SL000460) | P01880 | High | OS | 0.389 [0.227-0.668] | 0.0007 |
| TGM3 Protein-glutamine gamma-glutamyl-transferase E (SL008945) | Q08188 | Low | OS | 0.500 [0.292-0.855] | 0.012 |
| STX1A Syntaxin 1α (SL004304) | Q16623 | High | OS | 0.569 [0.331-0.977] | 0.04 |
| TK1 Thymidine kinase 1 (SL000057) | P04183 | High | OS | 0.491 [0.273-0.884] | 0.022 |
| IL17A Interleukin-17A (SL001713) | Q16552 | High | OS | 0.386 [0.215-0.693] | 0.0015 |
| PGF Placental growth factor (SL002640) | P49763 | High | PFS | HR of progression free survival (PFS) [CI 95%] 0.504 [0.314-0.810] | 0.0057 |

TABLE 2

Clinical outcome (here as determined by OS) dependent on the respective specific protein level under SoC treatment:

| Gene symbol (Somamer ID) | UniProt ID | High levels indicate good, or poor prognosis under SOC [HR] |
|---|---|---|
| TPO Thyroid peroxidase (SL000588) | P07202 | |
| CCL23.1 Chemokine (C-C motif) ligand 23 (SL003302) | P55773 | Poor [2.21] |
| IGHD_IGK._IGL. Immuno-globulin D (SL000460) | P01880 | Poor [2.38] |
| TGM3 Protein-glutamine gamma-glutamyl-transferase E (SL008945) | Q08188 | Good [0.656] |
| STX1A Syntaxin 1α (SL004304) | Q16623 | Poor [1.82] |

TABLE 2-continued

Clinical outcome (here as determined by OS) dependent on the respective specific protein level under SoC treatment:

| Gene symbol (Somamer ID) | UniProt ID | High levels indicate good, or poor prognosis under SOC [HR] |
|---|---|---|
| TK1 Thymidine kinase 1 (SL000057) | P04183 | Poor [1.15] |
| IL17A Interleukin-17A (SL001713) | Q16552 | Poor [1.64] |
| PGF Placental growth factor (SL002640) | P49763 | Poor [2.30] |

The clinical outcome of patients having tumors and/or metastases (both preferably also referred to as tumour lesions or lesions) is preferably analysed according to response (complete and partial), benefit (response and stable disease), and progressive disease. Lesions are preferably evaluated using Response Evaluation Criteria in Solid Tumors (i.e. RECIST criteria) whereby "complete response" (CR) is preferably defined as the disappearance of the target lesions; "partial response" (PR) is preferably defined as at least a 30% decrease in the sum of the longest iron metre of target lesions, preferably taking as reference the baseline sum longest diameter; "progressive disease" (PD) is preferably defined as at least a 20% increase in the sum of the longest diameter of target lesions, preferably taking as reference the smallest sum longest diameter recorded since the treatment started or the appearance of one or more new lesions; and "stable disease" (SD) is preferably defined as neither sufficient shrinkage to qualify for partial response nor sufficient increased to qualify for progressive disease, preferably taking as reference the smallest sum longest diameter since the treatment started.

Preferably, the at least one pan αv integrin inhibitor, preferably Abituzumab or Intetumumab (CNTO-95), is administered to said subject in combination with one or more chemotherapeutic agents.

Preferably, said one or more chemotherapeutic agents are selected from the group consisting of cetuximab, Panitumumab, irinotecan, vinorelbine, capecitabine, leucovorine, oxaliplatin, cisplatin, carboplatin, 5-fluorouracil (5-FU), bevacizumab, aflibercept and regorafenib.

Alternatively or additionally, one or more chemotherapeutic agents, a) selected from the group consisting of Leuproreline acetate, bicalutamide, nilutamide, triptoreline, gosereline, flutamide, cyproterone, busereline and degarelix, b) selected from the group consisting of Zoledronic acid, Pamidronic acid, Clodronate disodium, Alendronic acid and Ibandronic acid, and/or c) selected from the group consisting of Abiraterone, Abiraterone acetate, Prednisone, Enzalutamide, Radium Ra 223 dichloride, Docetaxel, Sipuleucel-T, Cabazitaxel and Mitoxantrone, can be employed.

Especially preferably, the at least one pan αv integrin inhibitor, preferably Abituzumab or Intetumumab (CNTO-95), more preferably Abituzumab, is administered to said subject in combination with two or more chemotherapeutic agents, preferably referred to as standards of care (SoC).

Preferred standards of care (SoC) include, but are not limited to:

the FOLFOX regimen, comprising 5-fluorouracil (5-FU), leucovorin (follinic acid) and oxaliplatin;

the FOLFIRI regimen, comprising folinic acid (leucovorin), fluorouracil (5-FU) and irinotecan; or the CAPDX regimen, comprising capecitabine and oxaliplatin.

Preferably, the FOLFOX regimen, the FOLFIRI regimen and the CAPDX regimen can be advantageously combined with:

anti-EGFR Therapy, preferably in kras wild-type patients, comprising or consisting of Cetuximab or Panitumumab, anti-VEGF Therapy, comprising or consiting of Bevacizumab or Aflibercept, or multi-kinase Therapy, comprising or consisting of Regorafenib.

More preferred standards of care (SoC) include, but are not limited to:

cetuximab in combination with irinotecan, cetuximab in combination with irinotecan and leucovorin, cetuximab in combination with irinotecan, 5-FU and leucovorin.

The cetuximab-containg regimen are preferred in subjects/patients having k-ras codon 2 wild-type cancer tissue status.

Especially preferred standards of care (SoC) include, but are not limited to:

Cetuximab in combination with irinotecan

Preferably, the cetuximab is administered to a subject in an amount of 400 mg/m$^2$ on Day 1 of the first cycle and afterwards in an amount of 250 mg/m$^2$ every two weeks.

Preferably, the irinotecan is administered to the subject in an amount of 180 mg/m$^2$ every two weeks.

However, the treatment of solid cancers and/or metastases thereof may involve surgery, radiation therapy including brachytherapy and external beam radiation therapy, high-intensity focused ultrasound (HIFU), chemotherapy, oral chemotherapeutic drugs (Temozolomide/TMZ), cryosurgery, hormonal therapy, or combinations thereof.

Most hormone dependent cancers become refractory after one to three years and resume growth despite hormone therapy. Previously considered "hormone-refractory cancer" or "androgen-independent cancer", the term castration-resistant has replaced "hormone refractory" because while they are no longer responsive to castration treatment (reduction of available androgen/testosterone/DHT by chemical or surgical means), these cancers still show reliance upon hormones for androgen receptor activation.

Chemotherapeutics in this respect preferably include, but are not limited to docetaxel, cabazitaxel, bevacizumab, docetaxel, thalidomide and prednisone, and combinations thereof. E.g., a combination of bevacizumab, docetaxel, thalidomide and prednisone has shown clinical benefits.

Luteinizing hormone-releasing hormone (LH-RH) agonists and/or antagonists as well as gonadotropin-releasing hormone (GnRH) agonists Luteinizing hormone-releasing hormone (LH-RH) are hormone therapy drugs that lower the production of testosterone in a man's body. This drop in testosterone usually slows or stops the growth of prostate cancer and/or the metastases thereof for a period of time.

Pain is common in metastatic cancers and especially in case of bone metastases thereof, and cancer pain related to bone metastases can be treated with bisphosphonates, medications such as opioids, and palliative radiation therapy to known metastases. Spinal cord compression can occur with metastases to the spine, and can be treated with steroids, surgery, or radiation therapy.

The traditional treatments for cancer are Radiotherapy and chemotherapy, usually in combination with one another. Scientists and pharmaceutical companies are researching drugs to target different types of cancer, including metastatic bone disease.

High-intensity focused ultrasound (HIFU) has CE approval for palliative care for bone metastasis. As an entirely side-effect free and non-invasive treatment, HIFU has been successfully applied in the treatment of cancer to destroy tumours of the bone, brain, breast, liver, pancreas, rectum, kidney, testes, and prostate.

One treatment option for bone metastases that has to be considered is treatment with bisphosphonates, often in combination of other chemotherapeutics and/or (anti-)hormonal treatment. Bisphosphonates have shown great promise in reducing bone cancer pain, bone destruction, and tumor growth.

Monthly injections of radium-223 chloride (as Xofigo, formerly called Alpharadin) have been approved by the FDA in May 2013 for castration-resistant prostate cancer (CRPC) with bone metastases.

Integrins affect a variety of cellular functions that influence tumor progression, metastases, and angiogenesis in animal models (Desgrosellier J S, et al. Nat Rev Cancer 2010; 10:9-22).

$\alpha v$ integrins are cell adhesion molecules involved in cell survival, proliferation, migration, and angiogenesis; they are deregulated in various cancer types (Legate K R, et al. Nat Rev Mol Cell Biol 2006; 7:20-31; Guise T A, et al. Clin Cancer Res 2006; 12:62135-16s).

Abituzumab is a humanized monoclonal IgG2 antibody that specifically targets all $\alpha v$ integrins (Mitjans F, et al. J Cell Sci 1995; 108:2825-38; Monnier Y, et al. Cancer Res 2008:68; 7323-31).

In colorectal cancer (CRC), integrin $\alpha v \beta 6$ is expressed on tumor Cells (Goodman S L, et al. Biol Open 2012; 1:329-40); $\alpha v \beta 6$ overexpression is associated with significantly reduced median overall survival (OS) in patients with advanced CRC (Bates R C, et al. J Clin Invest 2005; 115:339-47).

In human tumor xenograft models, antitumor activity was observed with abituzumab, and an enhanced antitumor effect was observed when abituzumab was combined with either cetuximab or irinotecan.

POSEIDON, an open-label, randomized, controlled, comparative, multicenter phase I/II study in patients with metastatic CRC (mCRC) who have failed first-line oxaliplatin therapy examining abituzumab in combination with the standard of care (SoC: cetuximab plus irinotecan), showed very interesting outcomes.

In this randomized, double-blind, placebo-controlled, phase II trial, a total of 216 patients were randomized 1:1:1 to receive
  a) standard of care (SoC), e.g. cetuximab plus irinotecan plus placebo,
  b) SoC as described under a) plus abituzumab 500 mg, or
  c) SoC as described under a) plus abituzumab 1000 mg.

This showed that in the ITT population, neither dose of abituzumab significantly improved median PFS or RR. However, a trend toward improved OS was observed (abituzumab 500 mg: 15.0 [95% CI 10.9-19.2] months, HR 0.83 [0.54-1.28] vs SOC; abituzumab 1,000 mg 14.4 [9.8-19.3] months, HR 0.80 [0.52-1.25] vs SOC; vs 11.6 [9.8-15.7] months for SOC), suggesting clinical activity.

Blood sampling for plasma protein analyses was scheduled pre-treatment. Plasma protein analyses (based on highly protein-specific aptamers [SomaLogic system]) were performed on samples taken from 197 patients prior to treatment in cycle 1.

The original set of simultaneously determined 1,129 plasma protein levels was restricted to 888 proteins on the data level to avoid potential bias due to cell lysis or platelet activation during plasma preparation. Nine global biomarker search analyses were carried out using different normalization procedures, data sets and biomarker dichotomization thresholds, with the aim of filtering specific proteins that are predictive biomarkers for Abituzumab therapy success. The judgement whether a distinct protein is a predictive biomarker was based on an assessment of outcome (OS or PFS) in dependence of treatment (SoC or Abituzumab) and biomarker levels (continuous levels, and dichotomized categories "high" and "low" using the median of the investigated patient population as a threshold). Statistical tests were carried out per protein to identify those proteins that can be considered as predictive. The statistical tests are prior art and comprised. Among other criteria, logrank tests on selected populations, as for example the biomarker "high" and biomarker "low" populations, for detection of differences in outcome (here OS and/or PFS) for different treatment groups (Abituzumab and SOC; threshold p<=0.05), and Cox regression models investigating dependence of outcome on the interaction effect between treatment and continuous marker levels (interaction term p<=0.05). Further, the prognosticity of the marker levels was assessed on the basis of the patient group receiving SOC therapy using logrank tests (threshold p<=0.05) for the "high" and "low" subgroups.

This process identified 8 biomarker specific proteins in the plasma. The characteristics in which it is judged that the 8 biomarker specific proteins identified are active and whether levels above or below the median are predictive and/or prognostic are shown in Table 1 and/or 2.

Plasma Protein Analyses

Pre-treatment samples with full SomaLogic data (888 genes) were available for 192 tumors (122 treated with abituzumab; 70 treated with SoC alone). Plasma levels of each of the identified biomarker specific plasma proteins predicted increased survival with abituzumab compared to SoC alone in either the patients with "high" or the patients with "low" levels of the protein, and most were prognostic for survival (see FIG. 1 and for representative curves for CCL23, which is associated with CRC prognosis via CCR18, see one or more of FIGS. 1-18 for other proteins).

Furthermore, analysis of the biological context of other markers indicated that markers related to known molecular interactions of abituzumab (bone metabolism modulation and angiogenesis) appear to predict OS and/or PFS with abituzumab therapy.

Thus, plasma levels of each of the identified biomarker plasma proteins were surprisingly found to be prognostic of survival and predicted increased survival and/or progression free survival with abituzumab compared to SoC alone.

Thus, the clinical study delivered data on the pharmacokinetics and immunogenicity of abituzumab, as well as enabled analyses in search of predictive biomarkers, and surprisingly provided specific predictive proteinlevels in body fluids, especially specific plasma protein levels that allow predicting the therapy outcome under treatment with at least one pan $\alpha v$ integrin inhibitor, preferably including the pan $\alpha v$ integrin inhibitor abituzumab.

Abituzumab is a monoclonal anti-alpha v antibody also designated herein as DI-17E6, DI17E6, EMR62242 and/or EMD 525797).

DI17E6 is an engineered specifically tailored IgG2 hybrid monoclonal antibody directed to alpha-v integrin (receptor). Cancer therapy by means of this antibody reduces side effects associated with this type of therapy, above all immune reactions, thereby reducing immunogenicity. The antibody is described in detail in WO 2009/010290, the disclosure of which is encorporated herein in its entirety.

Its hypervariable regions (CDRs) derive from murine mAb 17E6 (EMD 73034). This parent mouse IgG1 antibody is described, for example by Mitjans et al. (1995; J.Cell Sci. 108, 2825) and patents U.S. Pat. No. 5,985,278 and EP 719 859. Mouse mAb 17E6 is produced by hybridoma cell line 272-17E6 and deposited under accession number DSM ACC2160.

Its light chain domains derive from humanized monoclonal anti-EGFR antibody 425 (matuzumab). This antibody is described in detail for example in EP 0 531 47261, and derives from its murine counterpart 425 (mouse MAb 425, ATCC Hβ9629), The antibody was raised against the human A431 carcinoma cell line and found to bind to a polypeptide epitope on the external domain of the human epidermal growth factor receptor (EGFR). Matuzumab has shown in clinical trials high efficacy.

Generally DI17E6 as used according to the invention comprises:
  (i) a CDR light and a heavy chain region deriving from mouse monoclonal anti-αv integrin antibody 17E6
  (ii) a light chain framework region which is taken from humanized monoclonal anti-EGFR antibody 425,
  (iii) a heavy chain framework region deriving from mouse monoclonal anti-αv integrin antibody 17E6, optionally comprising one or more mutations of amino acids at specific positions, and
  (iv) a heavy chain constant region deriving from human IgG2 and a human constant kappa light chain region,
wherein in said IgG2 domain the IgG2 hinge region was replaced by the human IgG1 hinge domain, and;
wherein optionally one or more mutations within the IgG2 has been carried out.

Specifically, DI17E6 (designated as "DI-17E6γ2h (N297Q)" or "EMD 525797") as used for the treatment as claimed and in the clinical trials as described above and below, has the following amino acid sequence:
  (i) variable and constant light chain sequences (SEQ ID No. 1):

DIQMTQSPSSLSASVGDRVTITCRASQDISNYLAWYQQKPGKAPKLLIYYT

SKIHSGVPSRFSGSGSGTDYTFTISSLQPEDIATYYCQQGNTFPYTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC and
  (ii) variable and constant heavy chain sequences (SEQ ID No. 2):

QVQLQQSGGELAKPGASVKVSCKASGYTFSSFWMHWVRQAPGQGLEWIGYI

NPRSGYTEYNEIFRDKATMTTDTSTSTAYMELSSLRSEDTAVYYCASFLGR

-continued
GAMDYWGQGTTVTVSS<u>ASTKGPSVFPLAPCSRSTSESTAALGCLVKDYFPE

PVTVSWNSGALTSGVHTFPAVLQSSGLYSLSSVVTVPSSNFGTQTYTCNVD

HKPSNTKVDKTVEPKSSDKTHTCPPCPAPPVAGPSVFLFPPKPKDTLMISR

TPEVTCVVVDVSHEDPEVQFNWYVDGVEVHNAKTKPREEQAQSTFRVVSVL

TVVHQDWLNGKEYKCKVSNKGLPAPIEKTISKTKGQPREPQVYTLPPSREE

MTKNQVSLTCLVKGFYPSDIAVEWESNGQPENNYKTTPPMLDSDGSFFLYS

KLTVDKSRWQQGNVFSCSVMHEALHNHYTQKSLSLSPGK, wherein the underlined sequences represent the variable regions with the CDRs (in bold, identical with the parent mouse antibody). The modified IgG1 hinge region is represented by EPKSSDKTHTCPPCP (amino acids 217-231 of SEQ ID No. 2), and AQ is a substitution within the IgG2 domain.

However, as it was shown in WO 2009/010290, also variants of DI17E6 can be used according to the teaching of this invention. Thus, DI17E6 variants comprising one or more modifications within the heavy chain framework regions FR1:
(SEQ ID No. )
QVQLQQSGAELAEPGASVKMSCKASGYTFS FR2:
(SEQ ID No. 17)
WVKQRPGQGLEWIG FR3:
(SEQ ID No. )
KATMTADTSSSTAYMQLSGLTSEDSAVYYCAS FR4:
(SEQ ID No. 19)
WGQGTSVTVSS, wherein one or more of the bold and underlined positions are mutated, can be used in the treatment of prostate cancer patients as described. In more detail, the following position heavy chain framework region is mutated at one, more or all of the following positions can be mutated: A9, E13, M20, K38, R40, A72, S76, Q82, G85, T87, S91 and S113. These variants show the same or very similar biological activity and efficacy as compared to DI17E6 defined by its sequences above.

In general, the invention as described includes also modifications and variants of the DI17E6 antibody that are functionally and/or pharmaceutically identical or similar to unmodified DI17E6, and wherein the CDR regions and heavy and light chain variable regions are at least 80%, or at least 85%, or at least 90%, or at least 95% identical in their amino acid sequence compared to the respective variable regions of DI17E6. In addition, the invention also includes modifications and variants of the DI17E6 antibody that are functionally and/or pharmaceutically identical or similar to unmodified DI17E6, and wherein the constant regions are at least 80%, or at least 85%, or at least 90%, or at least 98% identical in their amino acid sequence compared to the respective constant regions of DI17E6. Changes is the constant regions of the IgG chains of the antibody may improve specific properties like immunogenicity, ADCC, and so on.

Thus, for use according the invention, also functional derivatives, biologically active variants or modifications of DI17E6 can be employed.

Accordingly, in the context of the presen invention, the terms "Abituzumab" and/or "DI17E6" preferably also comprise:
a biologically active variant or modification thereof that comprises the CDR regions and heavy and light chain variable regions, which are 80%-95% identical in amino acid sequence compared to the variable regions of Abituzumab;
a biologically active variant or modification that comprises a constant region, which is at least 80%-98% identical with the amino acid sequence compared to the constant region of Abituzumab;
an antibody that comprises one or more modifications within the heavy chain framework regions FR1:
(SEQ ID No. 16)
QVQLQQSGAELAEPGASVKMSCKASGYTFS FR2:
(SEQ ID No. 17)
WVKQRPGQGLEWIG FR3:
(SEQ ID No. 18)
KATMTADTSSSTAYMQLSGLTSEDSAVYYCAS FR4:
(SEQ ID No. 19)
WGQGTSVTVSS, wherein one or more of the bold and underlined positions are mutated and are different compared to the original respective sequence of abituzumab;
and/or
a modified DI17E6 antibody comprising a human IgG1 constant region instead of human IgG2, or a human IgG2 hinge region instead of the human IgG1 hinge.

Intetumumab or CNTO-95 is a human monoclonal antibody, preferably used in the treatment of solid tumors. It is also an anti-αv integrin antibody, which is preferably comprising human heavy chain and human light chain variable regions comprising the amino acid sequences as shown in SEQ ID NO: 6 and SEQ ID NO: 7 (in U.S. Pat. No. 7,550,142, Sequence 7 and Sequence 8, respectively), as shown below:

<210> SEQ ID NO 7
<211> LENGTH: 119
<212> TYPE: PRT
<213> ORGANISM: Homo sapiens

<400> SEQUENCE: 7

```
Gln Val Gln Leu Val Glu Ser Gly Gly Gly Val Val
1               5                   10
Gln Pro Gly Arg Ser Arg Arg Leu Ser Cys Ala Ala
            15                  20
Ser Gly Phe Thr Phe Ser Arg Tyr Thr Met His Trp
25                  30                      35
Val Arg Gln Ala Pro Gly Lys Gly Leu Glu Trp Val
                40                  45
Ala Val Ile Ser Phe Asp Gly Ser Asn Lys Tyr Tyr
            50                  55                  60
Val Asp Ser Val Lys Gly Arg Phe Thr Ile Ser Arg
                65                  70
Asp Asn Ser Glu Asn Thr Leu Tyr Leu Gln Val Asn
            75                  80
Ile Leu Arg Ala Glu Asp Thr Ala Val Tyr Tyr Cys
85                  90                      95
Ala Arg Glu Ala Arg Gly Ser Tyr Ala Phe Asp Ile
                100                 105
Trp Gly Gln Gly Thr Met Val Thr Val Ser Ser
            110                 115
```

<210> SEQ ID NO 8
<211> LENGTH: 108
<212> TYPE: PRT
<213> ORGANISM: Homo sapiens

<400> SEQUENCE: 8

```
Glu Ile Val Leu Thr Gln Ser Pro Ala Thr Leu Ser
1               5                       10
Leu Ser Pro Gly Glu Arg Ala Thr Leu Ser Cys Arg
            15                  20
Ala Ser Gln Ser Val Ser Ser Tyr Leu Ala Trp Tyr
25                  30                      35
Gln Gln Lys Pro Gly Gln Ala Pro Arg Leu Leu Ile
                40                  45
Tyr Asp Ala Ser Asn Arg Ala Thr Gly Ile Pro Ala
        50                  55                  60
Arg Phe Ser Gly Ser Gly Ser Gly Thr Asp Phe Thr
                    65                      70
Leu Thr Ile Ser Ser Leu Glu Pro Glu Asp Phe Ala
            75                  80
Val Tyr Tyr Cys Gln Gln Arg Ser Asn Trp Pro Pro
85                  90                      95
Phe Thr Phe Gly Pro Gly Thr Lys Val Asp Ile Lys
                100                 105
``` and/or
SEQ ID NO: 8 (in U.S. Pat. No. 7,163,681 as Sequence 7):

```
LOCUS       ABN29020 119 aa linear      PAT 07 FEB. 2007

DEFINITION  Sequence 7 from patent U.S. Pat. No. 7,163,681.

ACCESSION   ABN29020

VERSION     ABN29020.1 GI:125142205

DBSOURCE    accession ABN29020.1

KEYWORDS    .
```

```
SOURCE      Unknown.
ORGANISM    Unknown.
            Unclassified.
REFERENCE   1 (residues 1 to 119)
AUTHORS     Giles-Komar, J., Snyder, L., Trikha, M. and Nakada, M. T.
TITLE       Anti-integrin antibodies, compositions, methods and uses
JOURNAL     Patent: U.S. Pat. No. 7,163,681-A 7 16 JAN. 2007;
            Centocor, Inc.; Malvern, PA; US;
REMARK      CAMBIA Patent Lens: U.S. Pat. No. 7,163,681
FEATURES    Location/Qualifiers
source      1..119
            /organism = "unknown"
ORIGIN
  1         qvqlvesggg vvqpgrsrrl scaasgftfs rytmhwvrqa pgkglewvav isfdgsnkyy
 61         vdsvkgrfti srdnsently lqvnilraed tavyycarea rgsyafdiwg cigtmvtvss
//
```

SEQ ID NO: 9(in U.S. Pat. No. 7,163,681 as Sequence 8):

```
LOCUS       ABN29021 108 aa
linear      PAT 7 FEB. 2007
DEFINITION  Sequence 8 from U.S. Pat. No. 7,163,681.
ACCESSION   ABN29021
VERSION     ABN29021.1 GI:125142207
DBSOURCE    accession ABN29021.1
KEYWORDS    .
SOURCE      Unknown.
ORGANISM    Unknown.
            Unclassified.
REFERENCE   1 (residues 1 to 108)
AUTHORS     Giles-Komar, J., Snyder, L., Trikha, M. and Nakada, M. T.
TITLE       Anti-integrin antibodies, compositions, methods and uses
JOURNAL     Patent: U.S. Pat. No. 7,163,681-A 8 16 JAN. 2007; Centocor,
            Inc.; Malvern, PA; US;
REMARK      CAMBIA Patent Lens: U.S. Pat. No. 7,163,681
FEATURES    Location/Qualifiers
source      1..108
            /organism="unknown"
Region      2..107
            /region_name="IgV_L_kappa"
            /note="Immunoglobulin (Ig) light chain, kappa type,
            variable (V) domain; cd04980"
            /db_xref="CDD:143181"
Region      8..100
            /region_name="IG_like"
            /note="Immunoglobulin like; smart00410"
            /db_xref="CDD:214653"
Site        order(12,104,106..107)
            /site_type="other"
            /note="intrachain domain interface"
            /db_xref="CDD:143181"
```

```
Site            25..27
                /site_type="other"
                /note="L1 hypervariable region"
                /db_xref="CDD:143181"

Site            order(32,49,93)
                /site_type="other"
                /note="antigen binding site"
                /db_xref="CDD:143181"

Site            order(34,36,38,43,46,50,87)
                /site_type="other"
                /note="heterodimer interface [polypeptide binding]"
                /db_xref="CDD:143181"

Site            66..70
                /site_type="other"
                /note="L2 hypervariable region"
                /db_xref="CDD:143181"

Site            order(92..94,96..98)
                /site_type="other"
                /note="L3 hypervariable region"
                /db_xref="CDD:143181"

ORIGIN
  1             eivltqspat lslspgerat lscrasqsvs sylawyqqkp gqaprlliyd asnratgipa
 61             rfsgsgsgtd ftltisslep edfavyycqq rsnwppftfg pgtkvdik
//
```

Intetumumab is further characterised in WO02/12501 and U.S. Pat. No. 7,163,681, the disclosure of which is incorporated in their entirety into this application by reference.

Preferably, also functional derivatives, biologically active variants or modifications of Intetumumab can be employed in the instant invention.

For ease of use, the one or more proteins that are preferably active as biomarkers in the context of the present invention, i.e.

TPO (Somamer ID: SL000588; UniProt ID: P07202),
CCL23.1 (Somamer ID: SL003302; UniProt ID: P55773),
IGHD_IGK._IGL. (Somamer ID: SL000460; UniProt ID: P01880),
TK1 (Somamer ID: SL000057; UniProt ID: P04183),
IL17A (Somamer ID: SL001713; UniProt ID: 016552),
STX1A (Somamer ID: SL004304; UniProt ID: 016623), and
PGF (Somamer ID: SL002640; UniProt ID: P49763) and/or
TGM3 (UniProt ID: 008188), are preferably also referred to collectively as "specific proteins" or "said specific proteins" of the present invention, and preferably also referred to individuality as "the specific protein" or "said specific protein".

As used herein, the term "sequence homology" is understood by the ones skilled in the art, and methods for determining sequence homology are also known in the art.

As used herein, sequence homology is preferably determined using the BLAST algorithm. BLAST preferably stands for for Basic Local Alignment Search Tool and is an algorithm for comparing primary biological sequence information, such as the amino-acid sequences of different proteins or the nucleotides of DNA sequences. A BLAST search enables a researcher to compare a query sequence with a library or database of sequences, and identify library sequences that resemble the query sequence above a certain threshold. The BLAST algorithm and the computer program that implements it were developed by Stephen Altschul, Warren Gish, and David Lipman at the U.S. National Center for Biotechnology Information (NCBI), Webb Miller at the Pennsylvania State University, and Gene Myers at the University of Arizona. It is available on the web on the NCBI website. Alternative implementations include AB-BLAST (formerly known as WU-BLAST), FSA-BLAST (last updated in 2006), and ScalaBLAST.

Different types of BLASTs are available according to the query sequences. For example, following the discovery of a previously unknown gene in the mouse, a scientist will typically perform a BLAST search of the human genome to see if humans carry a similar gene; BLAST will identify sequences in the human genome that resemble the mouse gene based on similarity of sequence. The BLAST algorithm and program were designed by Stephen Altschul, Warren Gish, Webb Miller, Eugene Myers, and David J. Lipman at the NIH and was published in the Journal of Molecular Biology in 1990.

In the context of the present invention, the sequence homology of the proteins described herein is preferably determined using BLASTp.

In the context of the present invention, the sequence homology of the proteins described herein is more preferably determined on the basis of the longest local alignments generated using BLASTp.

In the context of the present invention, subjects and especially human subjects are preferably also referred to as patients.

As used herein, the term "about" with respect to numbers, amounts, dosings, hours, times, timings, durations, and the like, is preferably understood to mean "approximately" with respect to said numbers, amounts, dosings, hours, times, timings, durations, and the like. More Preferably, "about" means+/−10%, more preferably+/−5% of the given specific value with respect to numbers, amounts, dosings, hours, times, timings, durations, and the like.

If not specified otherwise, amounts administered to a subject, human subject or patient given in "mg", such as in 500 mg, 1000 mg, or the like, are preferably intended to mean the respective amounts to be administered "flat", i.e. as a fixed dose that is not adjusted to the bodyweight and/or body surface of the respective subject, human subject or patient.

If not explicitly indicated otherweise, the term "one or more" as used herein, e.g. with respect to the number of compounds, agents, cancer cotherapeutic agents, cancer chemotherapeutic agents and the like, preferably means "one or more than one" and thus preferably includes "two or more" (or "two or more than two"), "three or more" (or "three or more than three") and/or "four more" (or "more or more than four"). Accordingly, the term "one or more" as used herein preferably includes the numbers one, two, three, four, five, six and/or higher numbers. With respect to the number of agents, cancer cotherapeutic agents, cancer chemotherapeutic agents, it especially preferably includes the numbers one, two, three, four and/or five, even more preferably the numbers one, two, three and/or four and especially the numbers one, two and/or three.

Preferably, especially preferred subjects of the instant invention relate to aspects, subjects, uses, methods and/or embodiments, wherein one or more features of two or more of the herein described aspects, subjects, uses, methods and/or embodiments are combined in one subject.

The following examples are given in order to assist the skilled artisan to better understand the present invention by way of exemplification. The examples are not intended to limit the scope of protection conferred by the claims. The features, properties and advantages exemplified for the compounds and uses defined in the examples may preferably be assigned to other compounds and uses not specifically described and/or defined in the examples, but falling under the scope of what is defined in the claims.

The invention is explained in greater detail below by means of examples. The invention can be carried out throughout the range claimed and is not restricted to the examples given here.

Experimental Section

EXAMPLE 1

POSEIDON Clinical Study

POSEIDON, an open-label, randomized, controlled, comparative, multicenter phase I/II study in patients with metastatic CRC (mCRC) who have failed first-line oxaliplatin therapy examining abituzumab in combination with the standard of care (SoC: cetuximab plus irinotecan), showed very interesting outcomes.

In this randomized, double-blind, placebo-controlled, phase II trial, a total of 216 patients were randomized 1:1:1 to receive
  a) standard of care (SoC), e.g. cetuximab plus irinotecan plus placebo,
  b) SoC as described under a) plus abituzumab 500 mg, or
  c) SoC as described under a) plus abituzumab 1000 mg.

Pharmacokinetic Analysis
  Equal numbers of patients per arm were included in the pharmacokinetic analysis subgroup.
  Blood sampling for pharmacokinetic assessments was scheduled at various timepoints during cycles 1, 3, 4, 5, 6, and 7 of therapy.
  Pharmacokinetic parameters were calculated according to standard non-compartmental methods using the program KINETICA™ v4.1.1 (Innaphase).

Immunogenicity
  Blood sampling for immunogenicity was scheduled pre-dose in cycles 1, 3, 5 and 6, and at the end-of-treatment visit and safety follow-up visits.
  Generation of antibodies directed against abituzumab was evaluated centrally using a validated ELISA method.

Biomarker Analyses
  Archived tumor blocks or punch biopsy materials were collected to explore tumor expression of integrins and their ligands as well as proteins related to angiogenesis and the underlying disease, and their potential relationship to clinical outcomes.
    Availability of samples had to be confirmed at patient screening
    Analyses were performed using immunohistochemistry.
  Blood sampling for plasma protein analyses was scheduled pre-treatment.
  Plasma protein analyses (based on highly protein-specific aptamers [SomaLogic system]) were performed on samples taken from 197 patients prior to treatment in cycle 1
    The original set of simultaneously determined 1,129 plasma protein levels was restricted to 888 proteins on the data level to avoid potential bias due to cell lysis or platelet activation during plasma preparation
    Nine global biomarker search analyses were carried out using different normalization procedure, data sets and biomarker dichotomization thresholds, with the aim of filtering biomarker; criteria included data robustness and independence of specific biological annotations. The search process comprised a set of criteria ensuring that identified proteins are significantly ($p<0.05$) associated with outcome (here exemplary radiologic PFS) for either the patients with low or high levels. These tests comprise, among others, logrank tests for differences in survival (here PFS) for Abituzumab-treated/untreated patients in the biomarker-low and biomarker-high groups according to th median threshold, tests for an interaction effect on outcome (here PFS) between continuous marker levels and treatment based on Cox regression models.
    This process identified 8 biomarker active plasma proteins.

Results
Biomarker Analyses
The analysis process showed that in the ITT population:
Neither dose of abituzumab significantly improved median PFS or RR
A trend toward improved OS was observed (abituzumab 500 mg: 15.0 [95% CI 10.9-19.2] months, HR 0.83 [0.54-1.28] vs SOC; abituzumab 1,000 mg 14.4 [9.8-19.3] months, HR 0.80 [0.52-1.25] vs SOC; vs 11.6 [9.8-15.7] months for SOC), suggesting clinical activity
The overall safety profile of abituzumab combined with SoC was acceptable
High αvβ6 expression (above the median histoscore [median=70] of the population studied [n=197]) was negatively prognostic for OS in the SOC arm (n=65); it was also predictive f improved OS ((abituzumab 500 mg: 15.0 [95% CI 10.5-23.2] months, HR 0.55 [0.30-1.00] vs SOC; abituzumab 1,000 mg: not reached [9.7 months—not reached], HR 0.41 [0.21-0.81]; vs SOC: 10.2 [5.8-13.1] months) and RR (30.6% [16.3-48.1%]

vs 32.3% 16.7-51.4%] vs 16.1% [5.5-33.7%]) in patients treated with abituzumab.

Exploratory biomarker analyses comprised analyses of tumor expression of relevant markers by immunohistochemistry and plasma protein analyses.

Preplanned immunohistochemistry-based expression analyses of integrins αvβ3, αvβ5, αvβ6, αvβ8, and pan-αv were performed on primary tumor tissue Data were obtained for 197 of 216 patients enrolled.

Plasma protein analyses (based on highly protein-specific aptamers [SomaLogic system]) were performed on samples taken during pre-treatment patient screening.

After restricting the data to 888 of 1129 proteins not affected by CL/PA, nine global biomarker search analyses were carried out using different normalized data sets and different biomarker dichotomization thresholds This process identified 8 specific proteins in the plasma that are active as biomarker.

Plasma Protein Analyses

Pre-treatment samples with full SomaLogic data (888 genes) were available for 192 tumors (122 treated with abituzumab; 70 treated with SoC alone).

Figure 2:
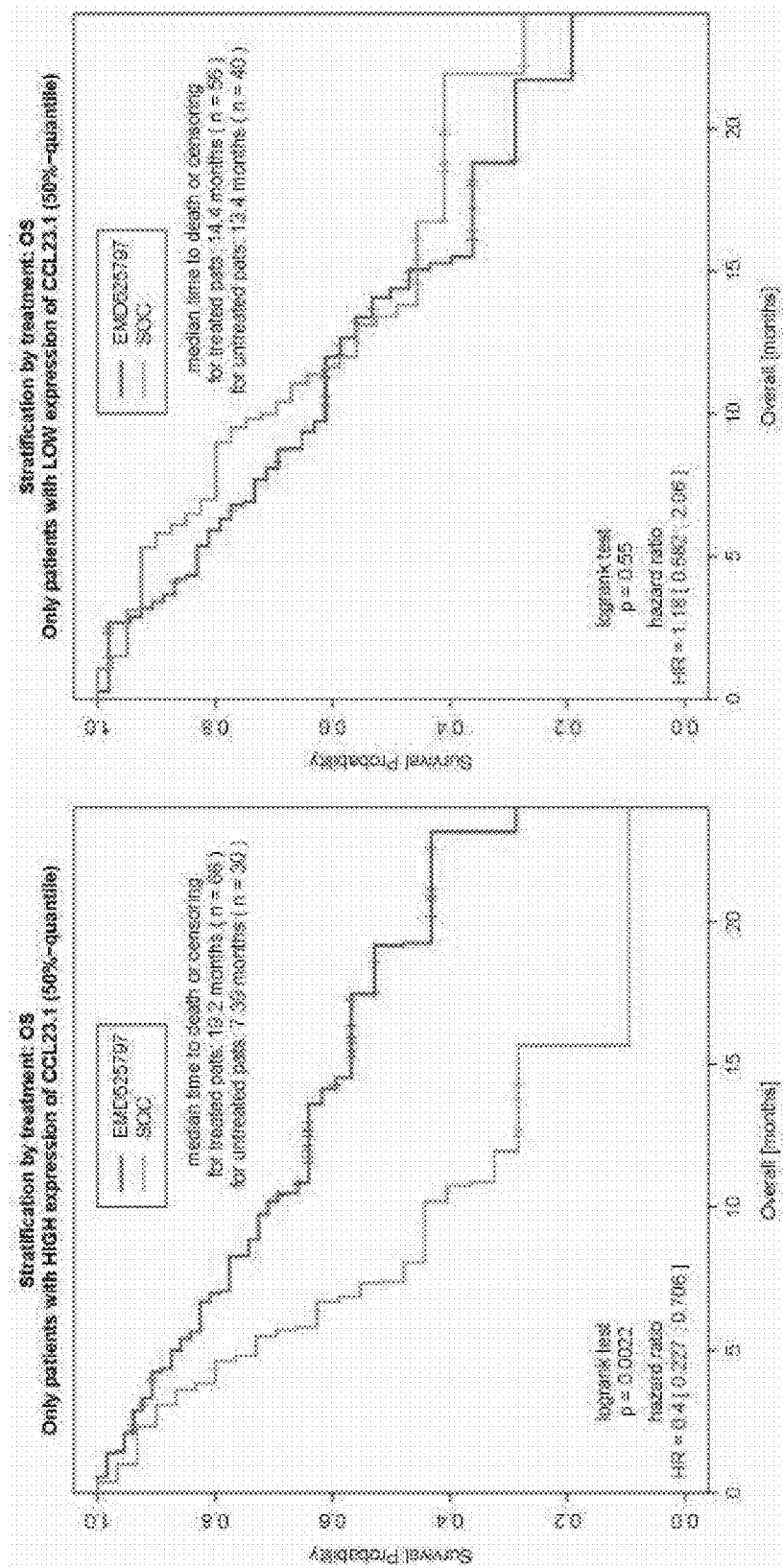
FIG. 2 shows a graph of the stratification by treatment of overall survival on patients with high expression of CCL23.1 and on patients with low expression of CCL23.1.
Figure 3:
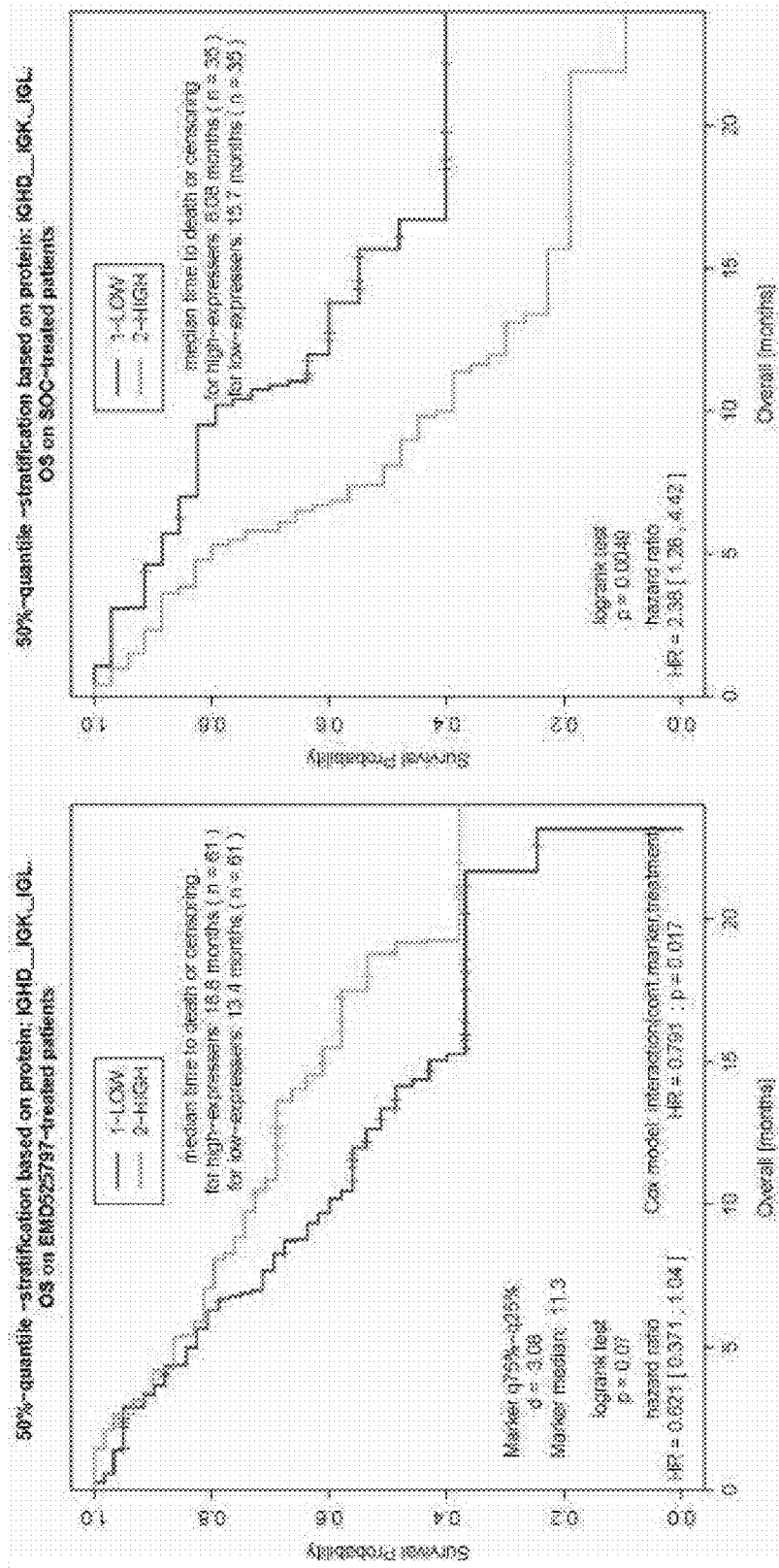
FIG. 3 shows a graph of the 50%-quantile stratification, based on protein IGHD_IGK.IGL., of overall survival on EMD525797-treated patients and on SOC-treated patients.
Figure 4:
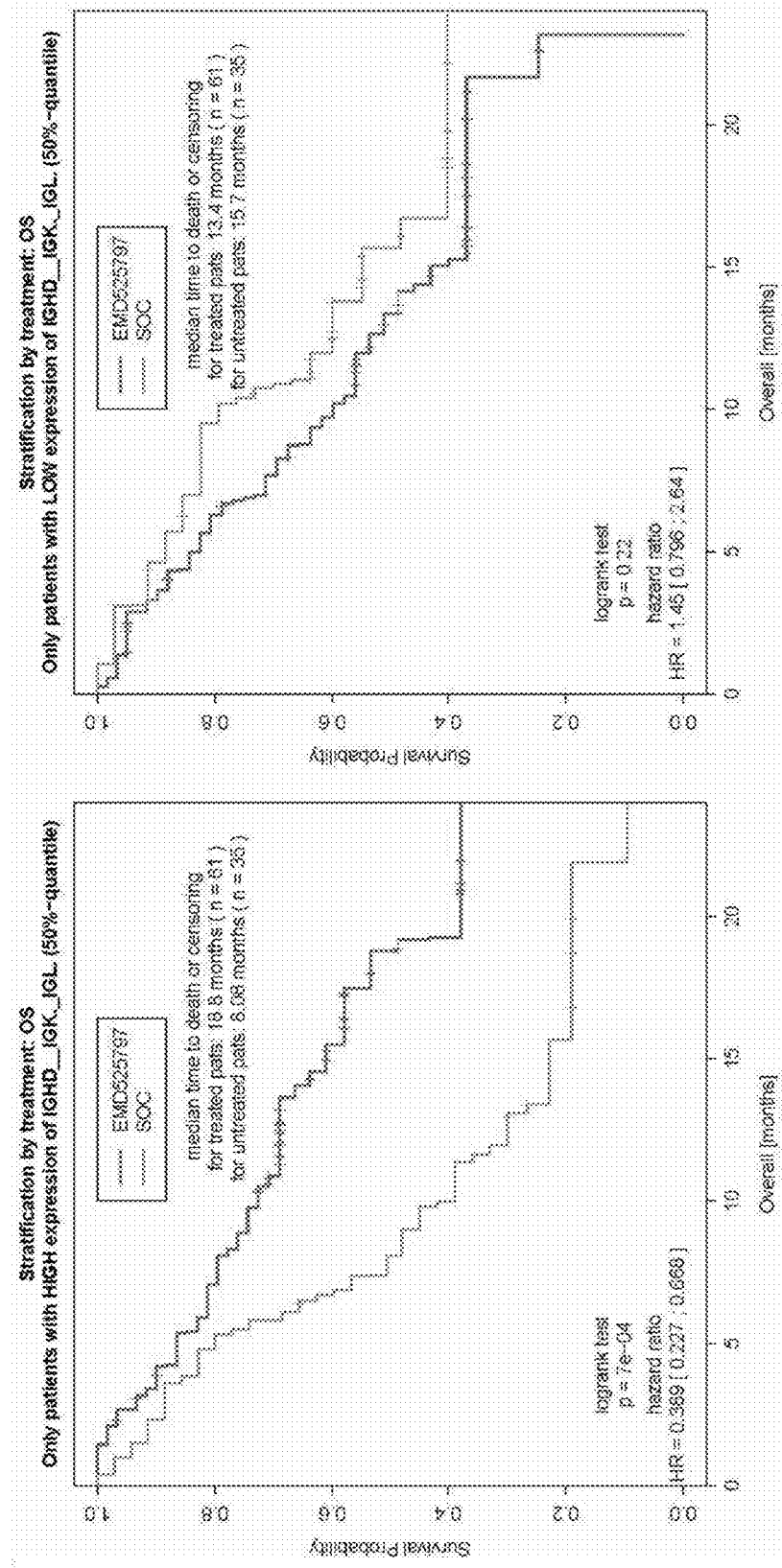
FIG. 4 shows a graph of the stratification by treatment of overall survival on patients with high expression of IGH-D_IGK.IGL. and on patients with low expression of IGH-D_IGK.IGL.
Figure 5:
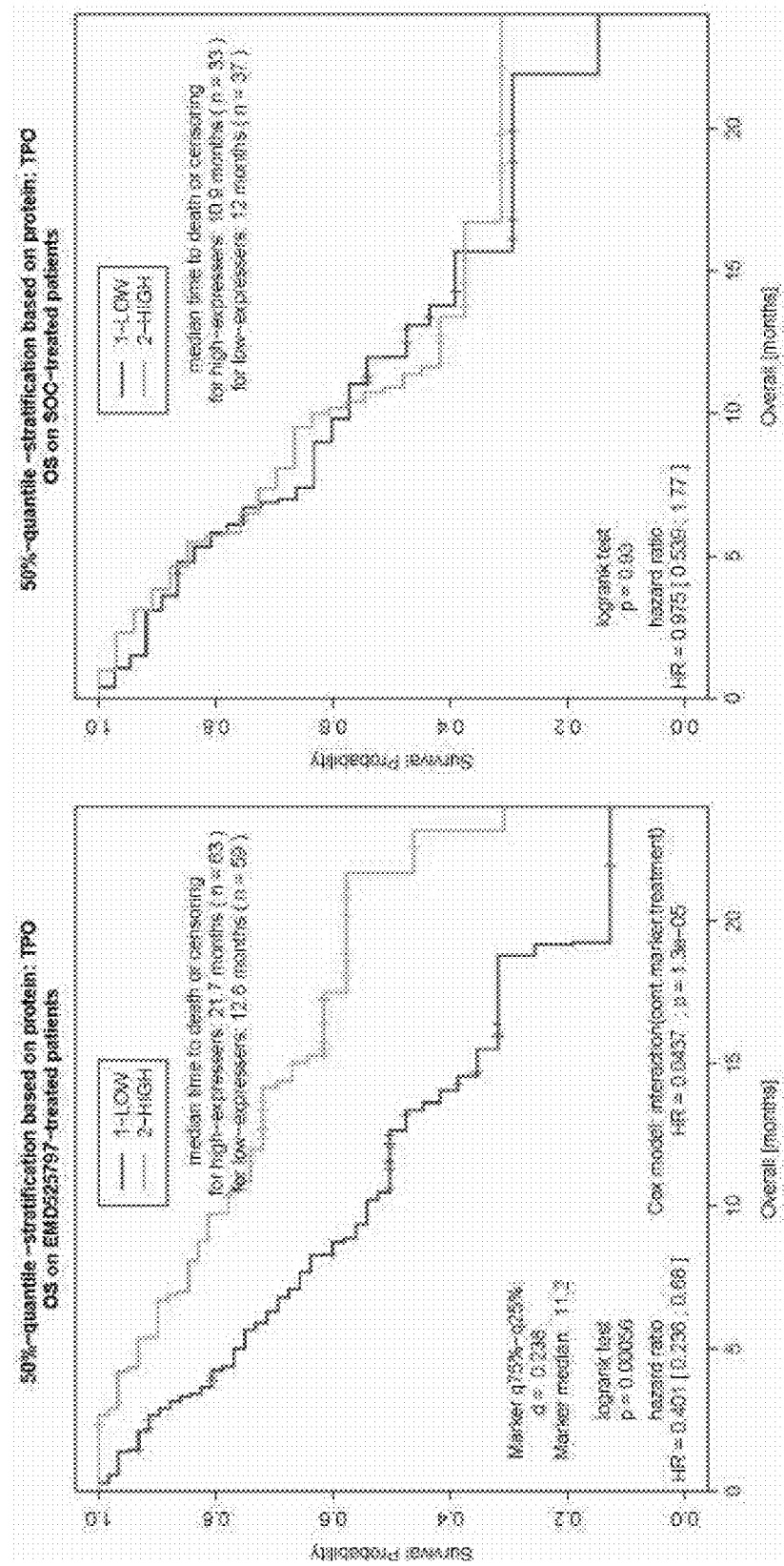
FIG. 5 shows a graph of the 50%-quantile stratification, based on protein TPO, of overall survival on EMD525797-treated patients and on SOC-treated patients.
Figure 6:
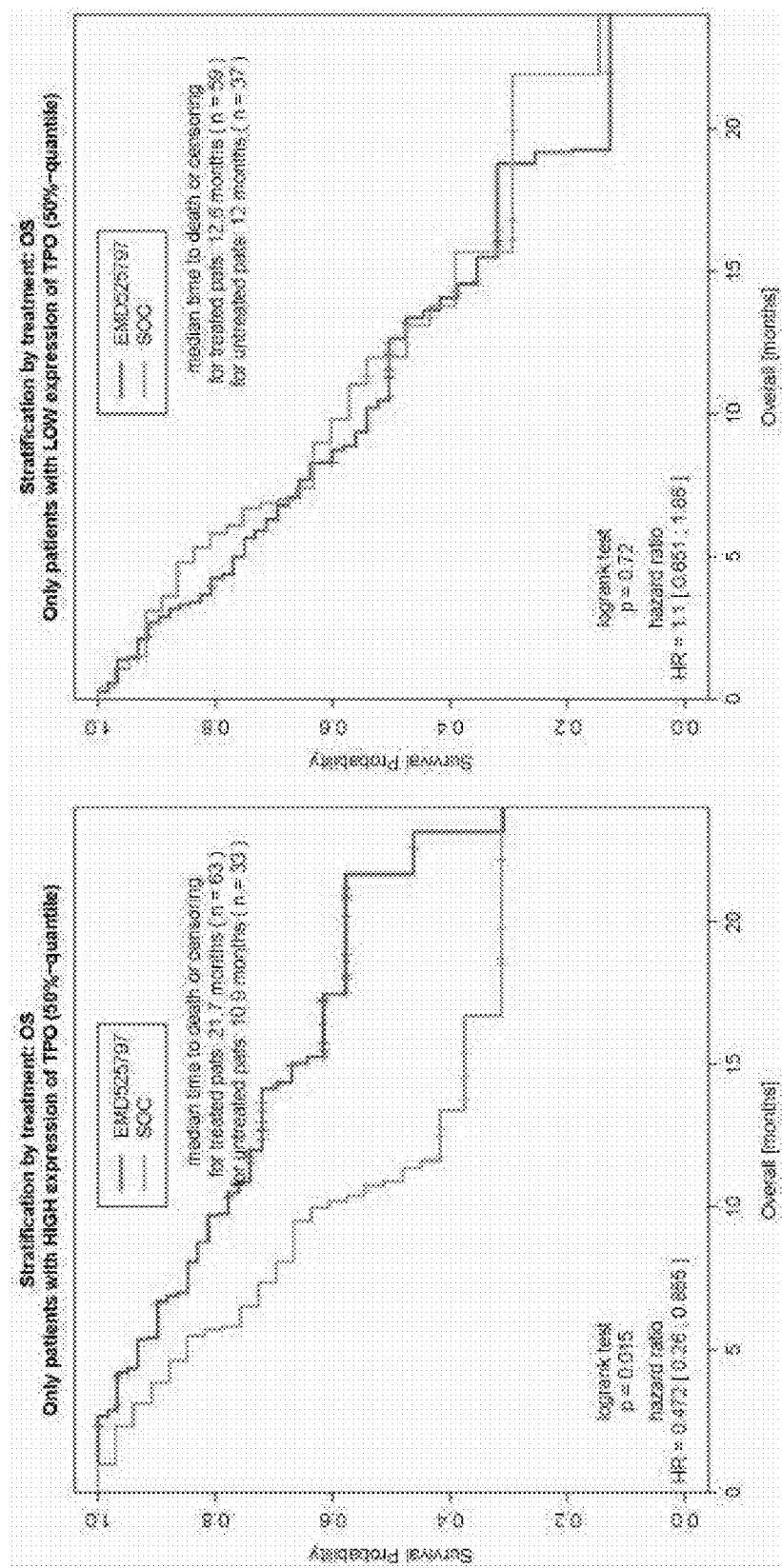
FIG. 6 shows a graph of the stratification by treatment of overall survival on patients with high expression of TPO and on patients with low expression of TPO.
Figure 7:
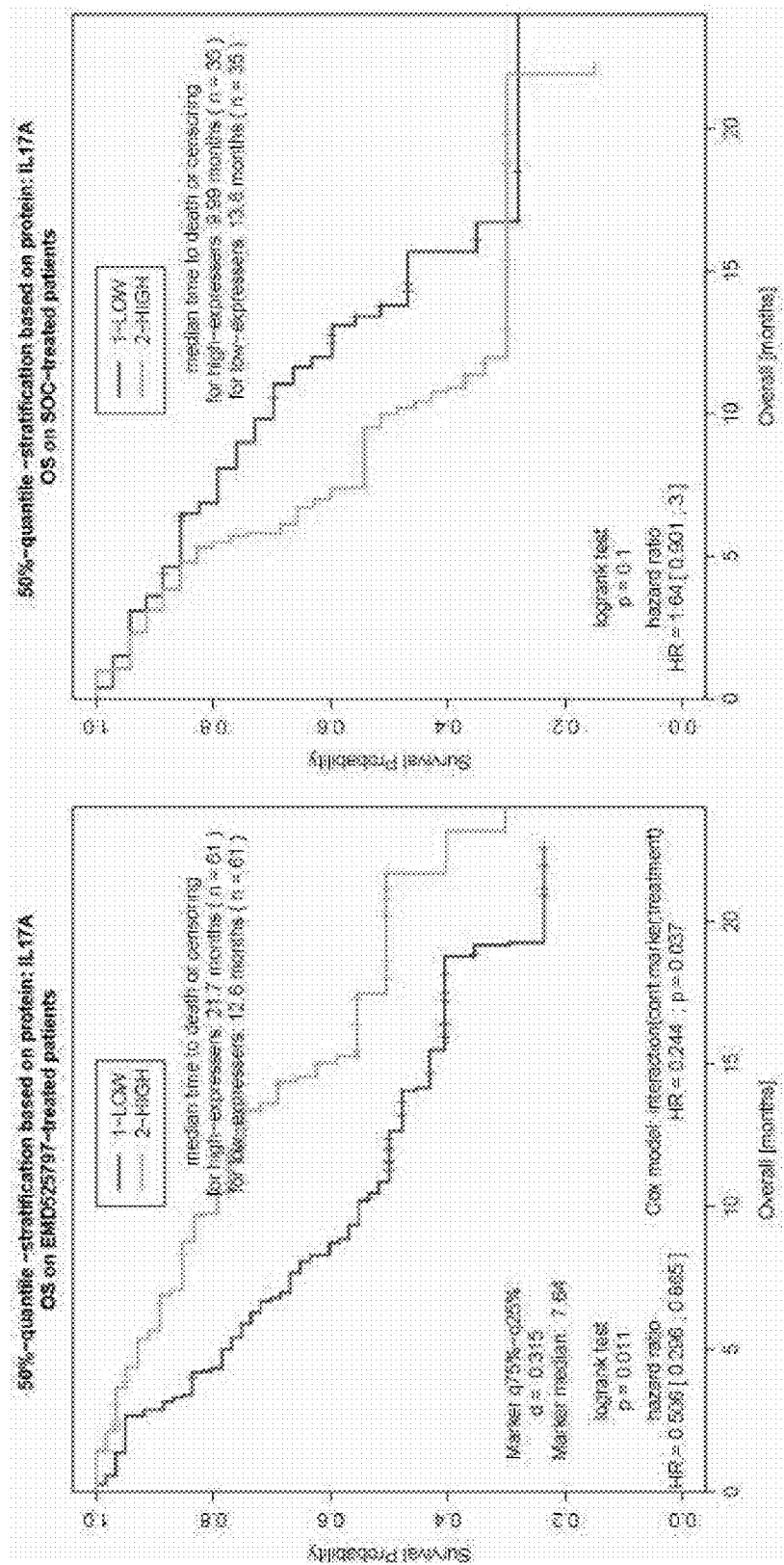
FIG. 7 shows a graph of the 50%-quantile stratification, based on protein IL17A, of overall survival on EMD525797-treated patients and on SOC-treated patients.
Figure 8:
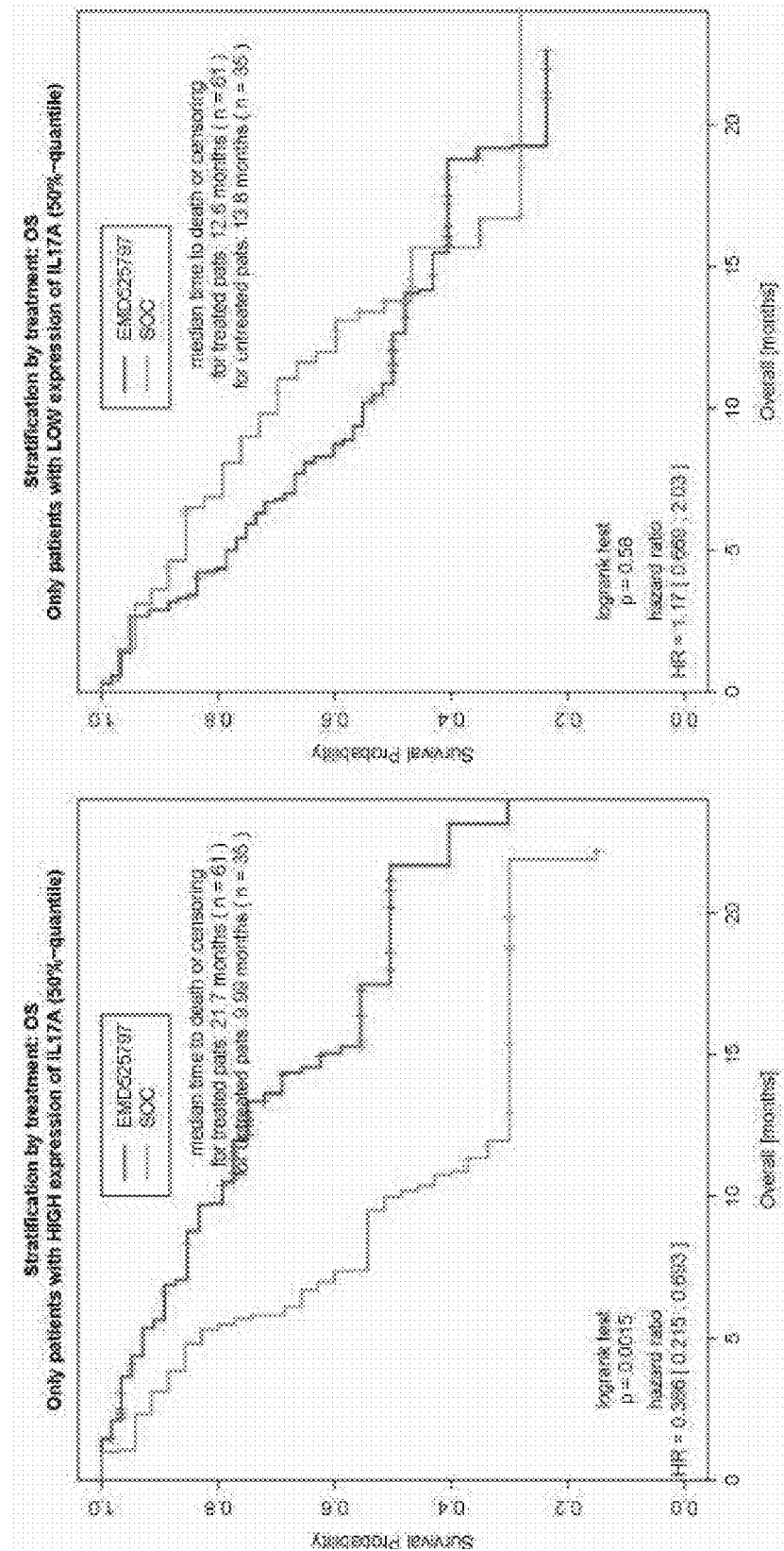
FIG. 8 shows a graph of the stratification by treatment of overall survival on patients with high expression of IL17A and on patients with low expression of IL17A.
Figure 9:
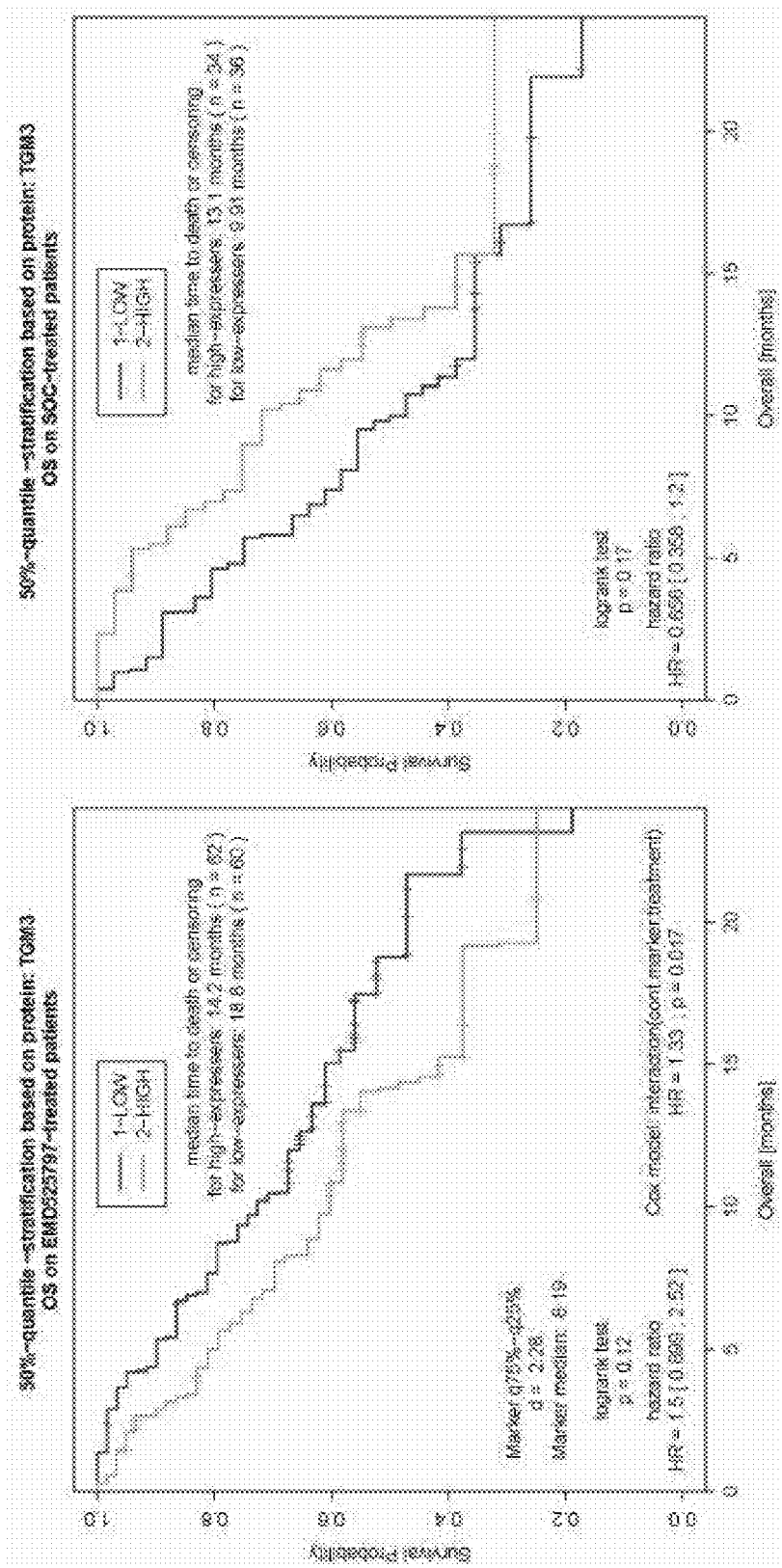
FIG. 9 shows a graph of the 50%-quantile stratification, based on protein TGM3, of overall survival on EMD525797-treated patients and on SOC-treated patients.
Figure 10:
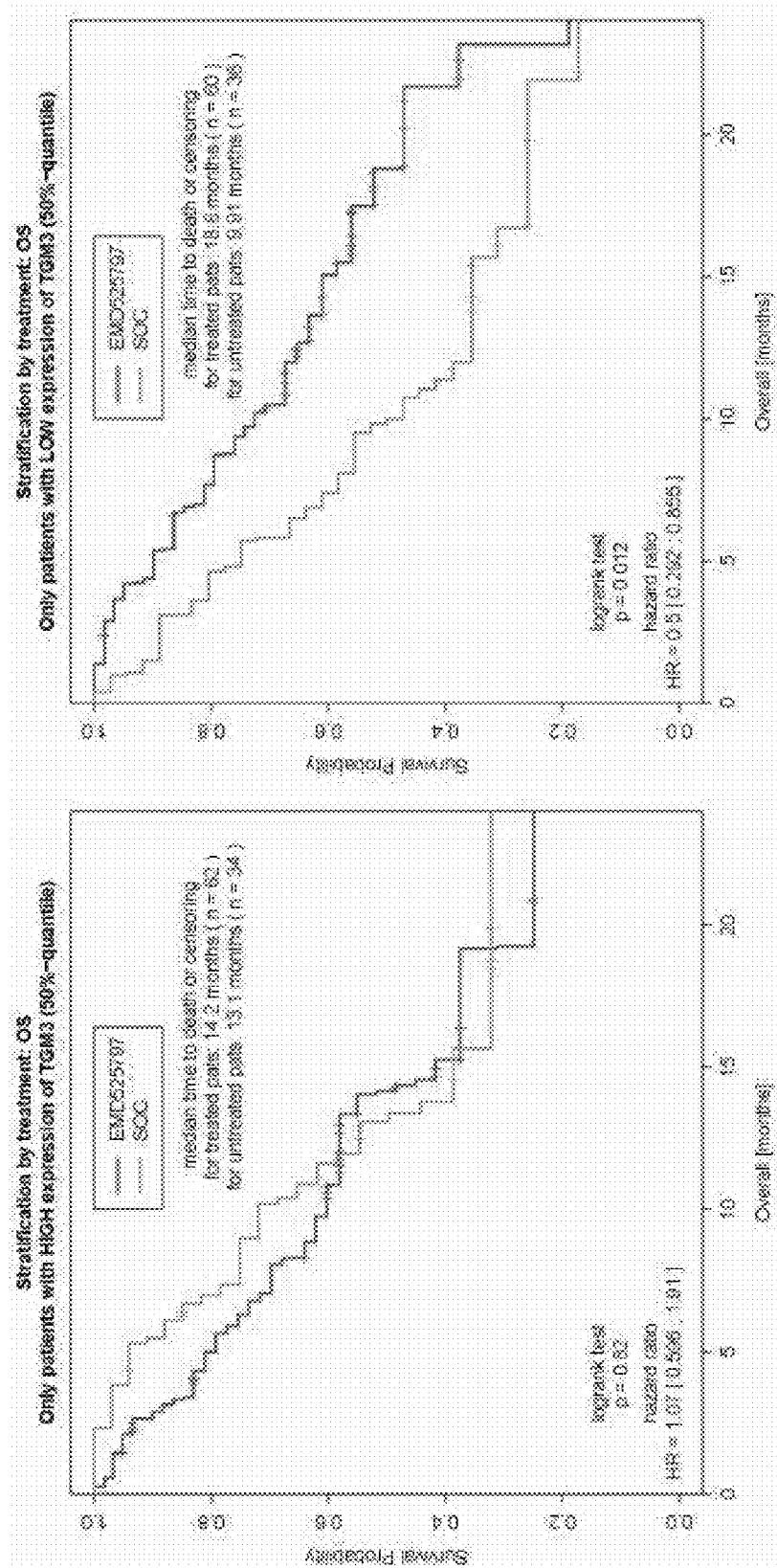
FIG. 10 shows a graph of the stratification by treatment of overall survival on patients with high expression of TGM3 and on patients with low expression of TGM3.
Figure 11:
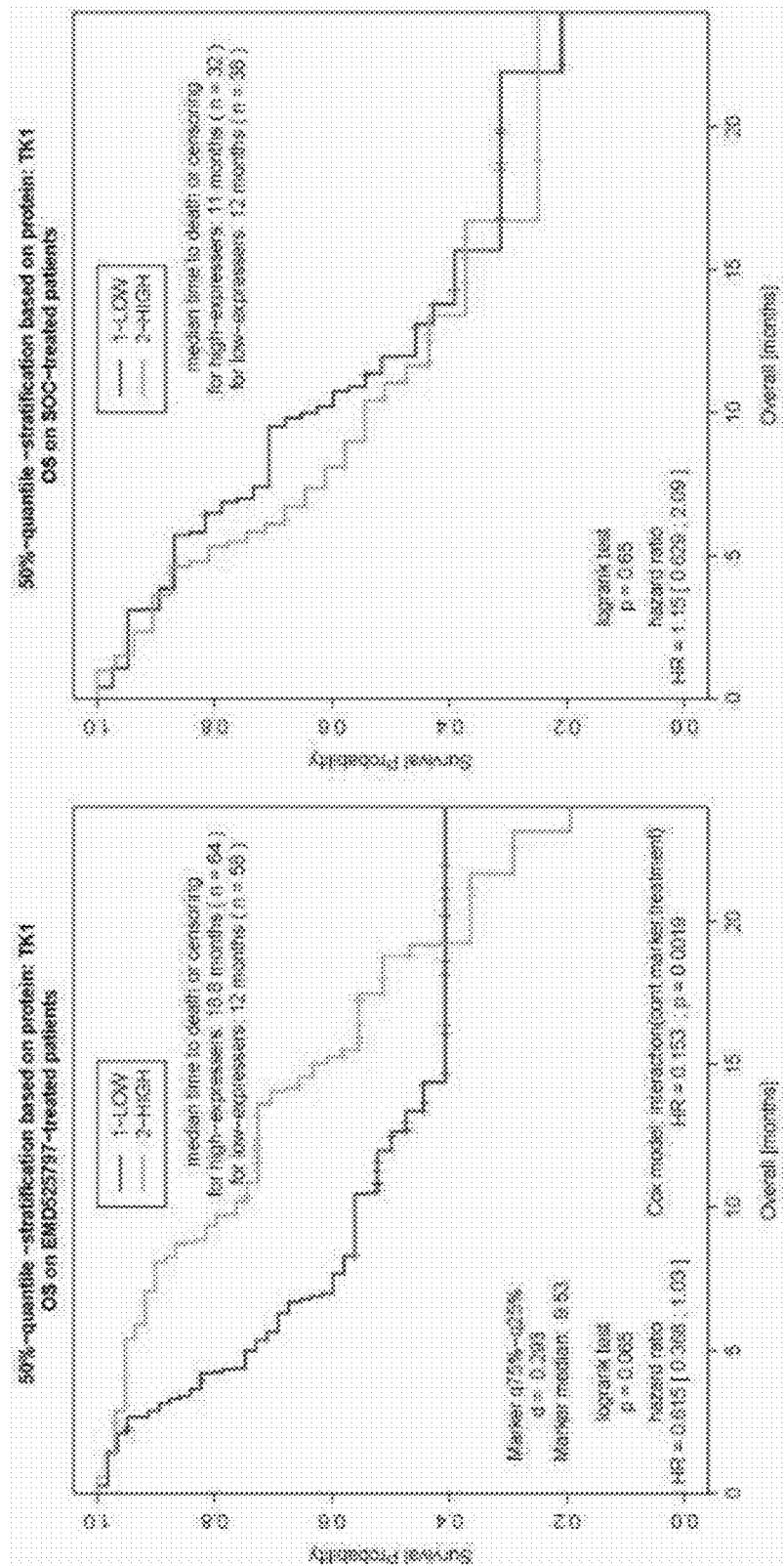
FIG. 11 shows a graph of the 50%-quantile stratification, based on protein TK1, of overall survival on EMD525797-treated patients and on SOC-treated patients.
Figure 12:
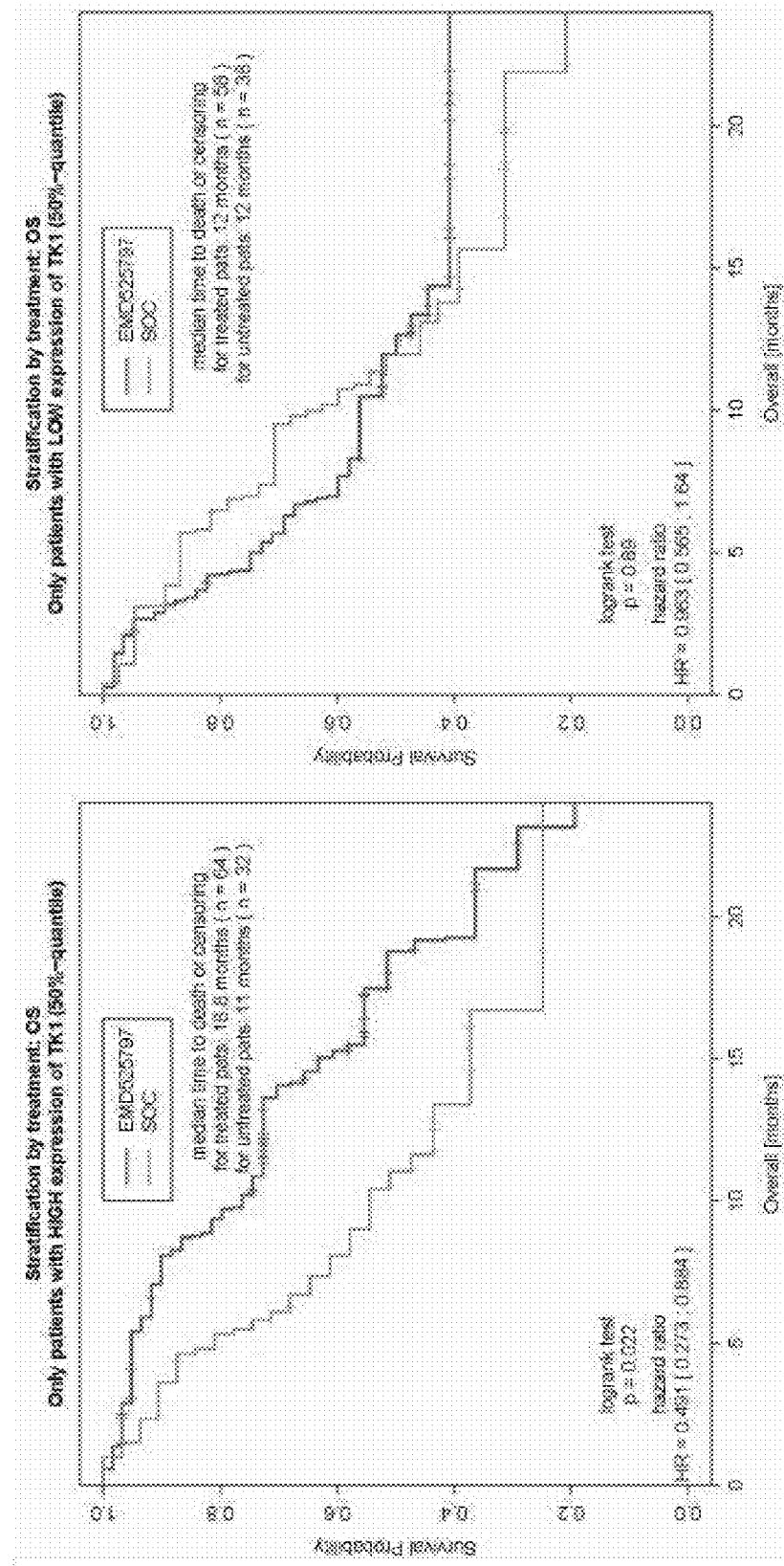
FIG. 12 shows a graph of the stratification by treatment of overall survival on patients with high expression of TK1 and on patients with low expression of TK1.
Figure 13:
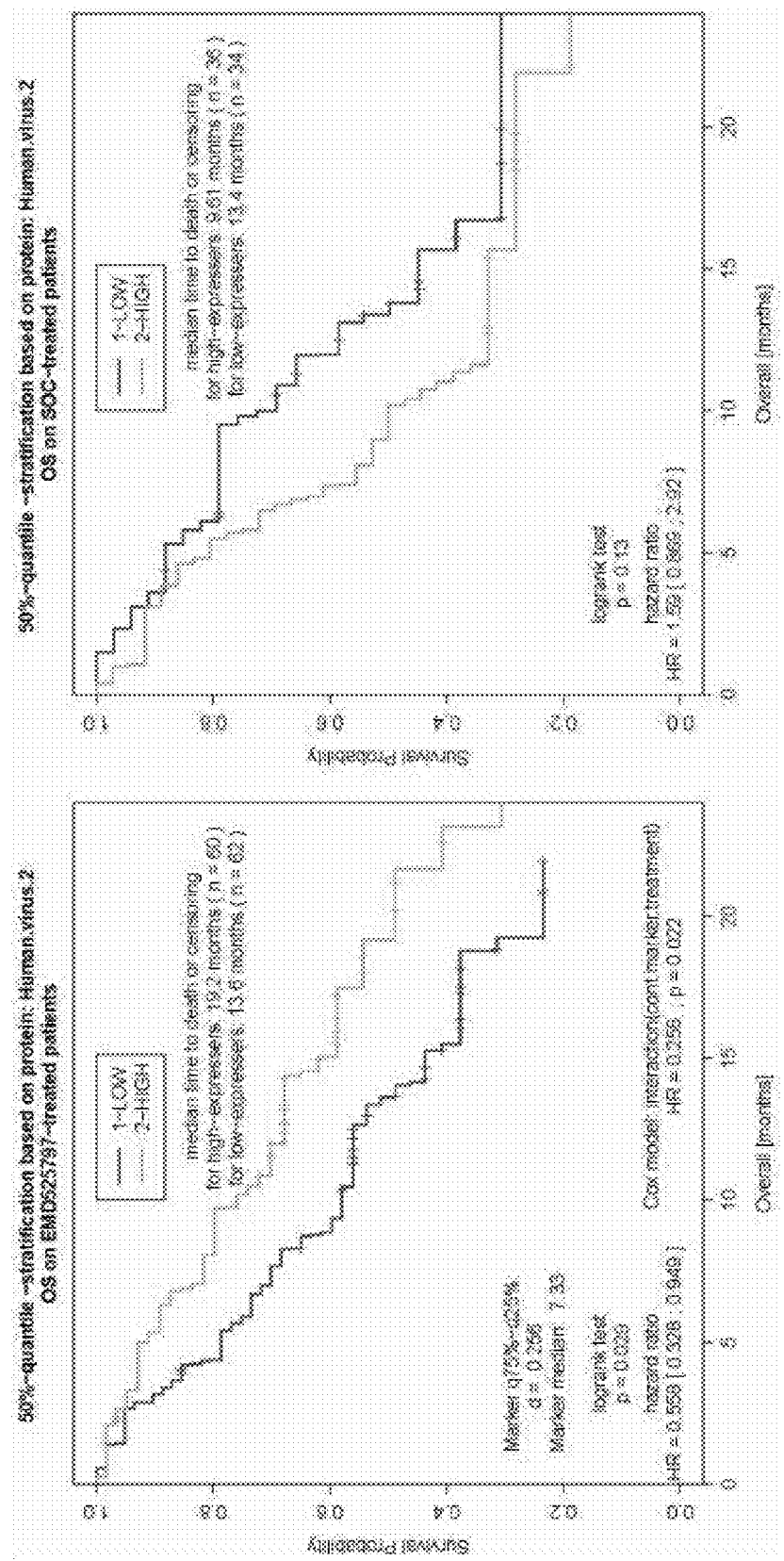
FIG. 13 shows a graph of the 50%-quantile stratification, based on protein Human.virus.2, of overall survival on EMD525797-treated patients and on SOC-treated patients.
Figure 14:
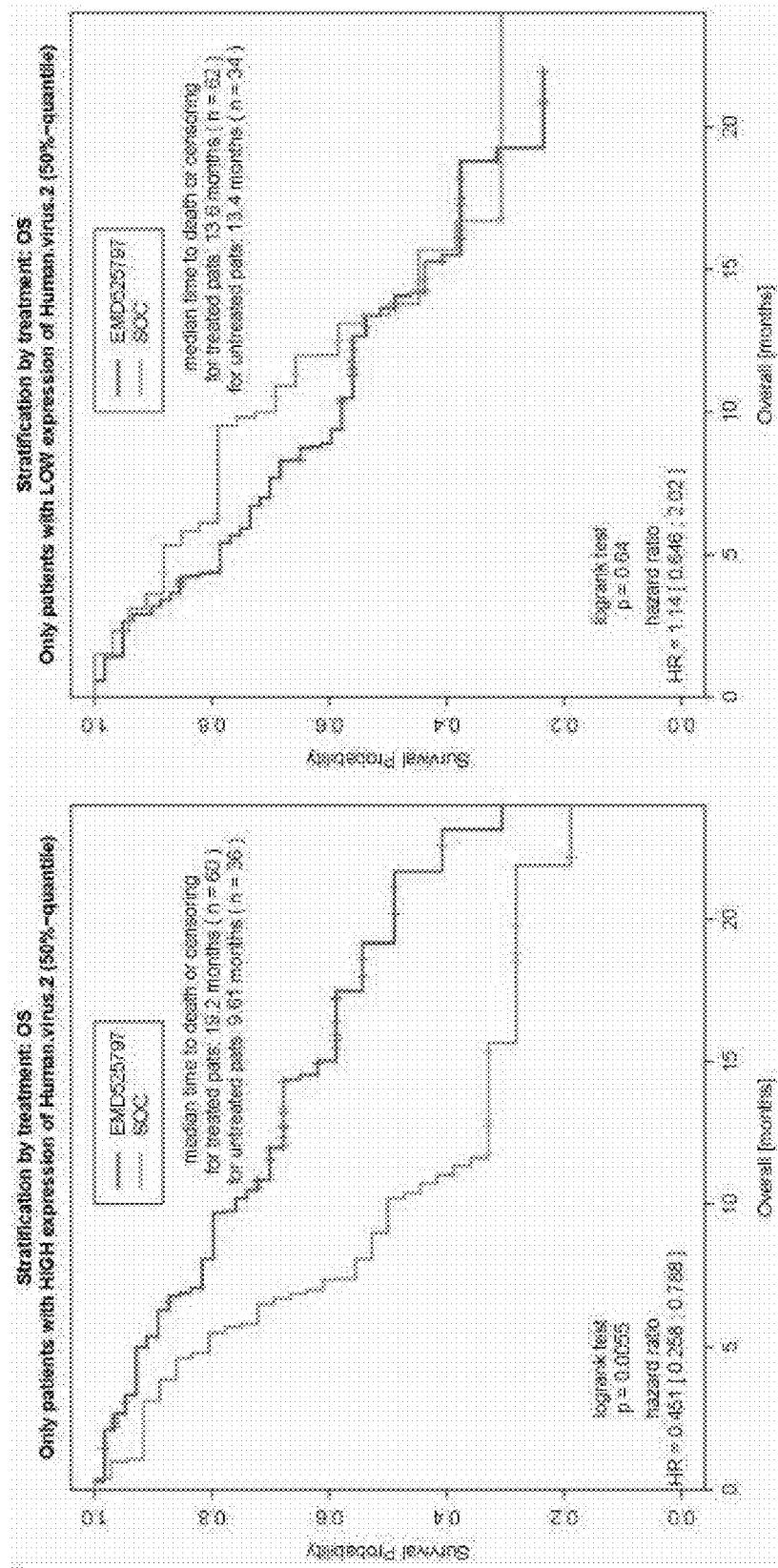
FIG. 14 shows a graph of the stratification by treatment of overall survival on patients with high expression of Human-.virus.2 and on patients with low expression of Human.virus.2.
Figure 15:
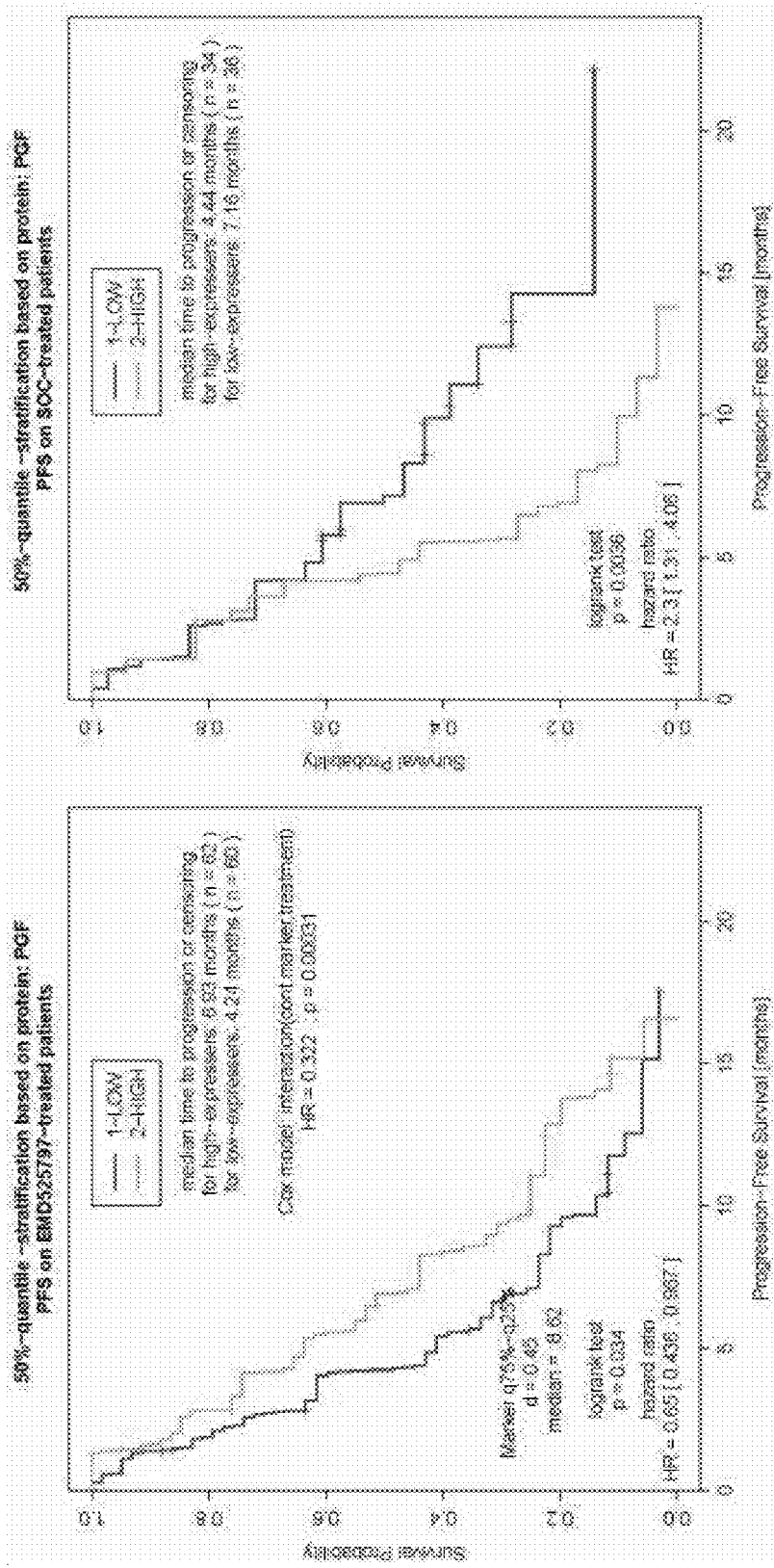
FIG. 15 shows a graph of the 50%-quantile stratification, based on protein PGF, of progression free survival on EMD525797-treated patients and on SOC-treated patients.
Figure 16:
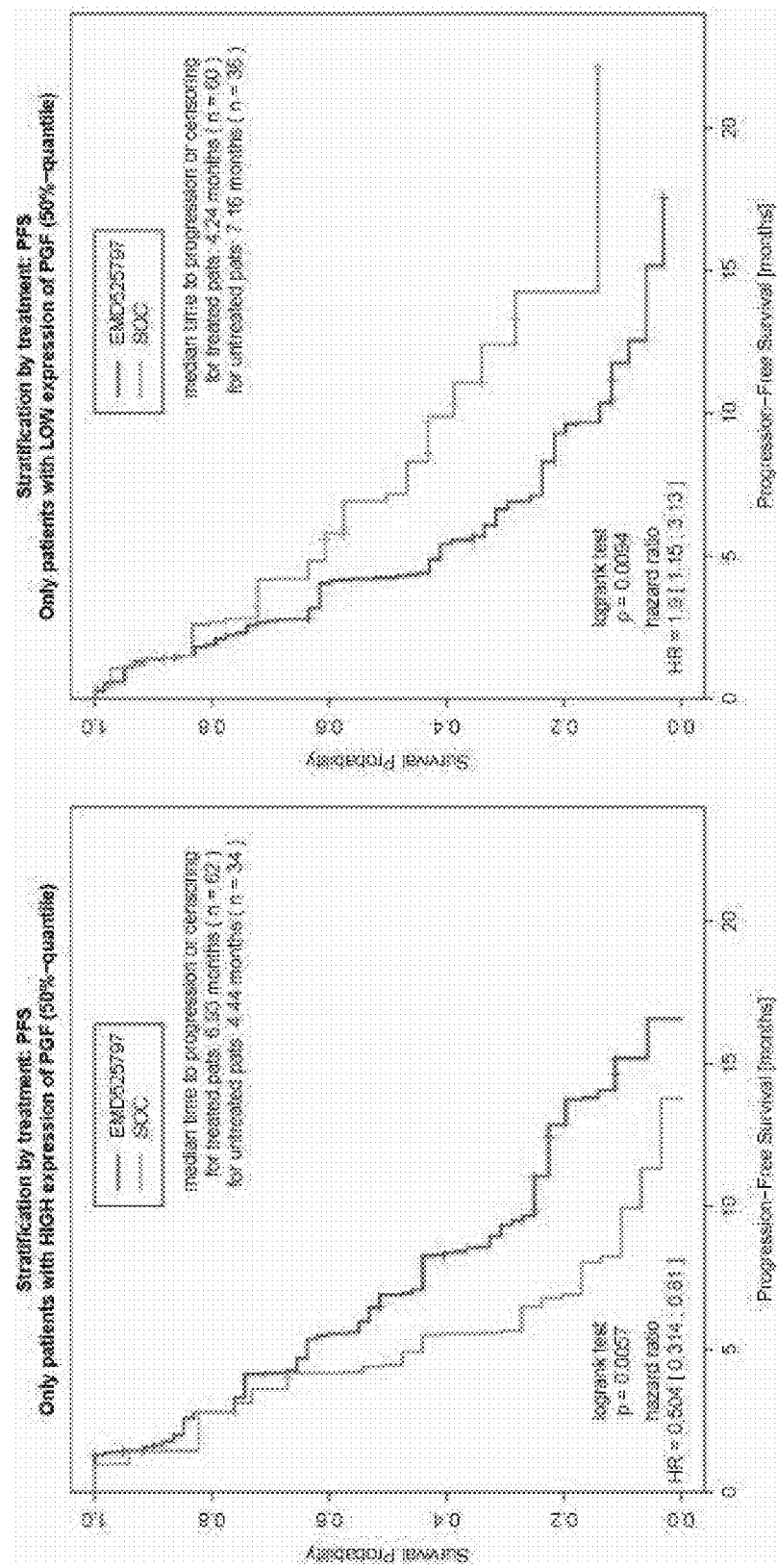
FIG. 16 shows a graph of the stratification by treatment of progress free survival on patients with high expression of PGF and on patients with low expression of PGF.
Figure 17:
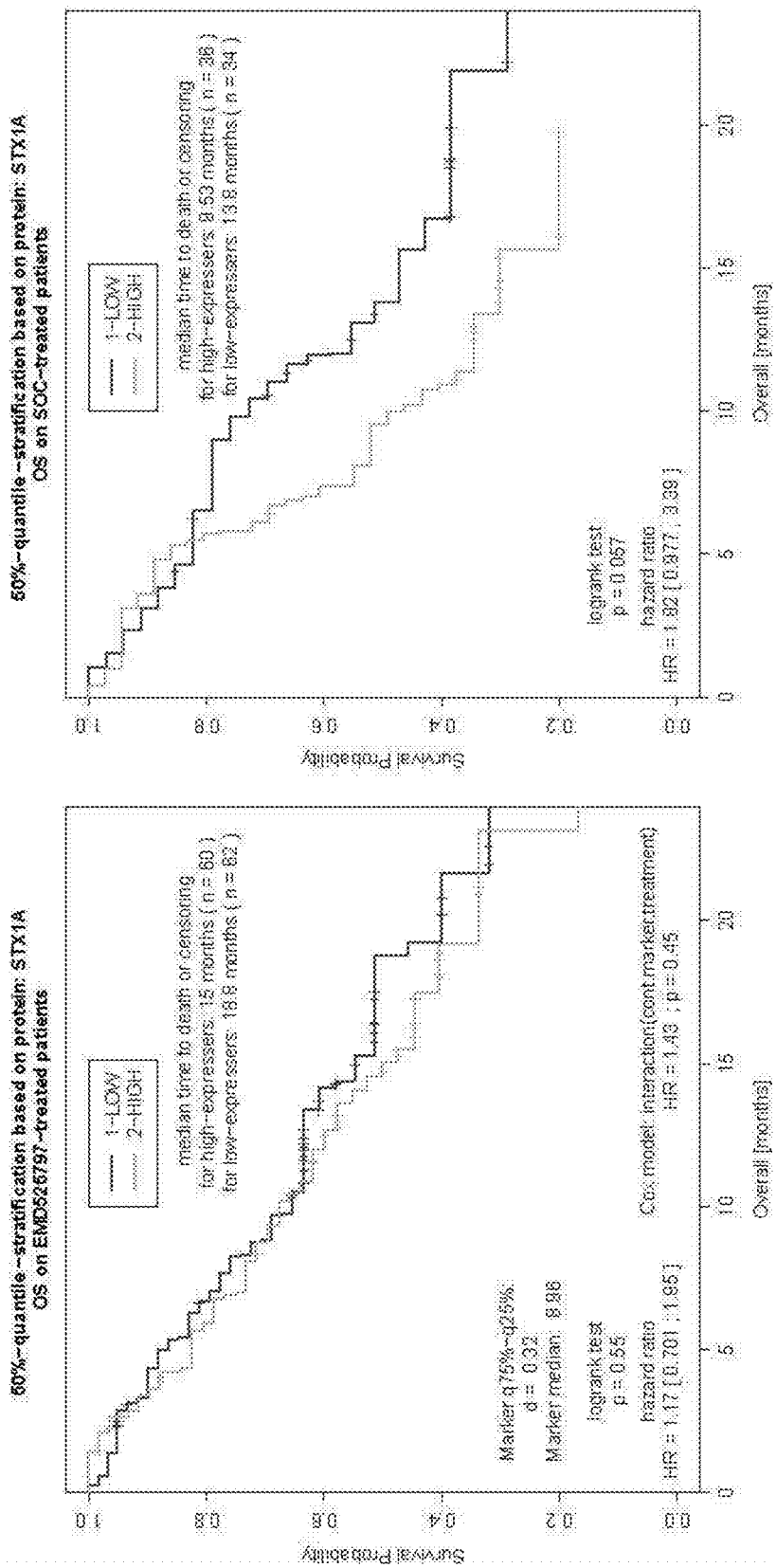
FIG. 17 shows a graph of the 50%-quantile stratification, based on protein STX1A, of overall survival on EMD525797-treated patients and on SOC-treated patients.
Figure 18:
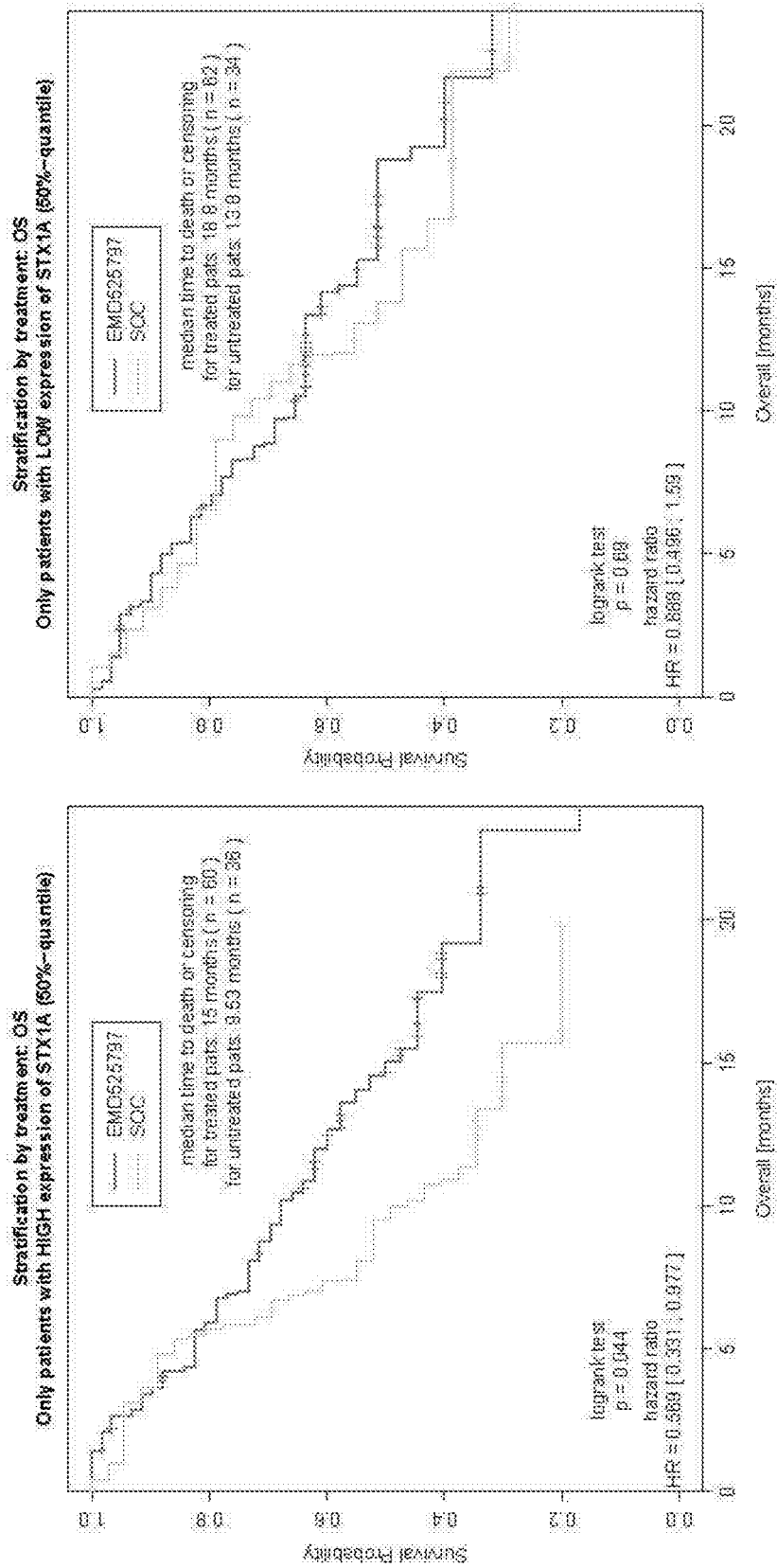
FIG. 18 shows a graph of the stratification by treatment of overall survival on patients with high expression of STX1A and on patients with low expression of STX1A.

Plasma levels of each of the identified biomarker active plasma proteins were prognostic of survival and predicted increased survival with abituzumab compared to SoC alone (see FIGS. 1 and 2 for representative curves for CCL23, which is associated with CRC prognosis via CCR18).

Thus, the analyses of the pre-treatment plasma protein levels identified 8 biomarker proteins that are predictive of OS and/or PFS, with the majority being also prognostic markers under SOC. These include CCL23, a ligand for CCR1, which appears to have a role in metastatic tumor growth and is associated with poor prognosis.

All identified 8 biomarker active plasma proteins are listed here:

TPO (Somamer ID: SL000588; UniProt ID: P07202),
CCL23.1 (Somamer ID: SL003302; UniProt ID: P55773),
IGHD_IGK._IGL. (Somamer ID: SL000460; UniProt ID: P01880),
TK1 (Somamer ID: SL000057; UniProt ID: P04183),
IL17A (Somamer ID: SL001713; UniProt ID: Q16552),
STX1A (Somamer ID: SL004304; UniProt ID: Q16623),
PGF (Somamer ID: SL002640; UniProt ID: P49763),
TGM3 (Somamer ID: SL008945; UniProt ID: Q08188).

Detailed results documenting the activity of the identified plasma proteins as predictive or prognostic, depending on levels above or below the median shown in Table 1, Table 2 and/or FIGS. 1 to 18.

EXAMPLE 2

Proteomic Affinity Assay Method

All steps of the proteomic affinity assay are performed at room temperature unless otherwise indicated.

Sample Thawing and Plating.

Aliquots of 100% serum or EDTA- plasma, stored at −80° C., are thawed by incubating in a 25° C. water bath for ten minutes. After thawing the samples are stored on ice during mixing and prior to sample dilution. Samples are mixed by gentle vortexing (setting # 4 on Vortex Genie, Scientific Industries) for 8 seconds. A 20% sample solution is prepared by transferring 16 µL of thawed sample into 96-well plates (Hybaid Omnitube 0.3 mL, ThermoFisher Scientific) containing 64 µL per well of the appropriate sample diluent at 4° C. Sample diluent for serum is 0.8x SB17 with 0.6 mM MgCl$_2$, 2 mM EGTA, 2 µM Z-Block_2, 0.05% TWEEN non-ionic surfactant and for EDTA-plasma is 0.8x SB18 with 0.8 mM MgCl$_2$, 2 mM EGTA, 2 µM Z-Block_2, 0.05% TWEEN non-ionic surfactant. This plate is stored on ice until the next sample dilution steps are initiated.

Preparation of 10%, 1% and 0.03% SOMAmer Solutions. SOMAmers are grouped into three unique mixes. The placing of a SOMAmer within a mix is empirically determined by assaying a dilution series of serum or plasma with each SOMAmer and identifying the sample dilution that gave the largest linear range of signal. The segregation of SOMAmers and mixing with different dilutions of sample (10%, 1% or 0.03%) allow the assay to span a $10^7$-fold range of protein concentration. The composition of the custom SOMAmer mixes is slightly different between plasma and serum as expected due to variation in protein composition of these two media. The custom stock SOMAmer solutions for 10%, 1% and 0.03% serum and plasma are prepared and stored at 8× concentration in SB17T. For each assay run, the three 8× SOMAmer solutions are diluted separately 1:4 into SB17T to achieve 2× concentration. Each diluted SOMAmer master mix is heated to 95° C. for five minutes and then to 37° C. for 15 minutes. 55 µL of each 2× SOMAmer mix is manually pipetted into a 96-well plate resulting in three plates with 10%, 1% or 0.03% SOMAmer mixes. After mixing with sample, the final individual SOMAmer concentration ranged from 0.25-4 nM for serum, 0.5 nM for plasma.

Equilibration. A 2% sample plate is prepared by diluting the 20% sample 1:10 into SB17T using the Beckman Coulter Biomek Fx$^P$ (Beckman Coulter). A 0.06% sample plate is prepared by diluting the 2% sample plate 1:31 into SB17T. The three sample dilutions are then transferred to their respective SOMAmer solutions by adding 55 µL of the sample to 55 µL of the appropriate 2× SOMAmer mix. The plates are sealed with a foil seal (Microseal 'F' Foil, Bio-Rad) and incubated at 37° C. for 3.5 hours.

Preparation of Catch-1 Bead Plates. 133.3 µL of a 7.5% Streptavidin-agarose bead slurry in SB17T is added to each well of three pre-washed 0.45 um filter plates. Each well of beads is washed once with 200 µL SB17T using vacuum filtration to remove the wash and then resuspended in 200 µL SB17T.

Catch-1 Bead Capture. All subsequent steps are performed by the Beckman Coulter Biomek Fx$^P$ robot unless otherwise noted. After the 3.5 hour equilibration, 100 µL of the 10%, 1% and 0.03% equilibration binding reactions is transferred to their respective Catch-1 Streptavidin agarose filter plates and incubated with shaking for ten minutes. Unbound solution is removed via vacuum filtration. Each set of Catch-1 beads is washed with 190 µL of 100 µM biotin in SB17T and then 190 mL of SB17T using vacuum filtration to remove the wash. 190 µL SB17T is added to each well in the Catch-1 plates and incubated with shaking for ten minutes at 25° C. The wash is removed via vacuum filtration and the bottom of the filter plates blotted to remove droplets using the on-deck blot station.

Biotinylation of Proteins. An aliquot of 100 mM NHS-PEO4-biotin in DMSO is thawed at 37° C. for six minutes and diluted to 1 mM with SB17T at pH 7.25. 100 µL of the NHSPEO4-biotin is added to each well of each Catch-1 filter plate and incubated with shaking for five minutes. Each biotinylation reaction is quenched by adding 150 µL of 20 mM glycine in SB17T to the Catch-1 plates with the NHS-PEO4-biotin. Plates are incubated for one minute with shaking, vacuum filtrated, and 190 µL 20 mM glycine SB17T is added to each well in the plate. The plates are incubated for one minute, shaking before removal by vacuum filtration. 190 µL of SB17T is added to each well and removed by vacuum filtration. The wells of the Catch-1 plates are subsequently washed three times by adding 190 µL SB17T, incubating for one minute with shaking followed by vacuum filtration. After the last wash the plates are centrifuged at 1000 rpm for one minute over a 1 mL deep-well plate to remove extraneous volume before elution. Centrifugation is performed off deck.

Kinetic Challenge and Photo-Cleavage. 85 µL of 10 mM dextran sulfate in SB17T is added to each well of the filter plates. The filter plates are placed onto a Thermal Shaker (Eppendorf) under a BlackRay light source and irradiated for ten minutes with shaking. The photo-cleaved solutions are sequentially eluted from each Catch-1 plate into a common deep well plate by centrifugation at 1000 rpm for one minute each.

Catch-2 Bead Capture. In bulk, MYONE™-Streptavidin C1 beads are washed two times for 5 minutes each with equal volume of 20 mM NaOH and three times with an equal volume of SB17T. Beads are resuspended in SB17T to a concentration of 10 mg/mL. After resuspension, 50 µL of this solution is manually pipetted into each well of a 96-well plate and stored at 4° C. until Catch-2. During Catch-2, the wash supernatant is removed via magnetic separation. All of the photo-cleaved eluate is pipetted onto the MYONE™-Streptavidin C1 magnetic beads and incubated with shaking at 25° C. for five minutes. The supernatant is removed from the MYONE™-Streptavidin C1 beads via magnetic separation and 75 µL of SB17T is transferred to each well. The plate is mixed for one minute at 37° C. with shaking and then 75 µL of 60% glycerol (in SB17T) at 37° C. is transferred to each well. The plate is mixed for another minute at 37° C. with shaking. The wash is removed via magnetic separation. These washes are repeated two more times. After removal of the third glycerol wash from the MYONE™-Streptavidin C1 beads, 150 µL of SB17T is added to each well and the plates incubated at 37° C. with shaking for one minute before removal by magnetic separation. The MYONE™-Streptavidin C1 beads are washed a final time using 150 µL SD19T with incubation for one minute, prior to magnetic seperation.

Catch-2 Bead Elution and Neutralization.

SOMAmers are eluted from MYONE™-Streptavidin C1 beads by incubating each well of beads with 105 µL of 100 mM CAPSO pH 10, 1 M NaCl, 0.05% TWEEN non-ionic surfactant with shaking for five minutes. 90 µL of each eluate is transferred during magnetic separation to a new 96-well plate containing 10 µL of 500 mM HCl, 500 mM HEPES, 0.05% TWEEN non-ionic surfactant pH 7.5.

Hybridization. 20 µL of each neutralized Catch-2 eluate is transferred to a new 96-well plate and 5 µL of 10x Agilent Block (Oligo aCGH/ChIP-on-chip Hybridization Kit, Large Volume, Agilent Technologies 5188-5380), containing a 10x spike of hybridization controls (10 Cy3 SOMAmers) is added to each well. After removing the plate from the robot, 25 µL of 2x Agilent Hybridization buffer (Oligo aCGH/ChIP-on-chip Hybridization Kit, Agilent Technologies) is manually pipetted to the each well of the plate containing the neutralized samples and blocking buffer. 40 µL of this solution is manually pipetted into each "well" of the hybridization gasket slide (Hybridization Gasket Slide - 8 microarrays per slide format, Agilent Technologies). Custom Agilent microarray slides containing 10 probes per array complementary to 40 nucleotide selected region of each SOMAmer with a 20x dT linker are placed onto the gasket slides according to the manufacturer's protocol. Each assembly (Hybridization Chamber Kit - SureHyb™ enabled, Agilent Technologies) is tightly clamped and loaded into a hybridization oven for 19 hours at 60° C. rotating at 20 rpm.

Post-Hybridization Washing. Approximately 400 mL Wash Buffer 1 (Oligo aCGH/ChIP-on-chip Wash Buffer 1, Agilent Technologies) is placed into each of two separate glass staining dishes. Six of the twelve slide/gasket assemblies are sequentially disassembled into the first staining dish containing Wash Buffer 1.

Once disassembled, the slide is quickly transferred into a slide rack in a second staining dish containing Wash Buffer 1. The slides are incubated for five minutes in Wash Buffer 1 with mixing via magnetic stir bar. The slide rack is then transferred to the 37° C. Wash Buffer 2 (Oligo aCGH/ChIP-onchip Wash Buffer 2, Agilent Technologies) and allowed to incubate for five minutes with stirring. The slide rack is transferred to a fourth staining dish containing acetonitrile and incubated for five minutes with stirring.

Microarray Imaging. The microarray slides are imaged with a microarray scanner (Agilent G2565CA Microarray Scanner System, Agilent Technologies) in the Cy3-channel at 5 µm resolution at 100% PMT setting and the XRD option enabled at 0.05. The resulting tiff images are processed using Agilent feature extraction software version 10.5.1.1 with the GE1_105_Dec08 protocol.

SEQUENCE LISTING

```
<160> NUMBER OF SEQ ID NOS: 18

<210> SEQ ID NO 1
<211> LENGTH: 214
<212> TYPE: PRT
<213> ORGANISM: Artificial Sequence
<220> FEATURE:
<223> OTHER INFORMATION: DI17E6 light chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45
```

Tyr Tyr Thr Ser Lys Ile His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210

<210> SEQ ID NO 2
<211> LENGTH: 447
<212> TYPE: PRT
<213> ORGANISM: Artificial Sequence
<220> FEATURE:
<223> OTHER INFORMATION: DI17E6 heavy chain

<400> SEQUENCE: 2

Gln Val Gln Leu Gln Gln Ser Gly Gly Glu Leu Ala Lys Pro Gly Ala
1               5                   10                  15

Ser Val Lys Val Ser Cys Lys Ala Ser Gly Tyr Thr Phe Ser Ser Phe
                20                  25                  30

Trp Met His Trp Val Arg Gln Ala Pro Gly Gln Gly Leu Glu Trp Ile
            35                  40                  45

Gly Tyr Ile Asn Pro Arg Ser Gly Tyr Thr Glu Tyr Asn Glu Ile Phe
    50                  55                  60

Arg Asp Lys Ala Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Phe Leu Gly Arg Gly Ala Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
                195                 200                 205

Asn Thr Lys Val Asp Lys Thr Val Glu Pro Lys Ser Ser Asp Lys Thr
210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Ala Gln Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 3
<211> LENGTH: 30
<212> TYPE: PRT
<213> ORGANISM: Artificial Sequence
<220> FEATURE:
<223> OTHER INFORMATION: heavy chain framework region

<400> SEQUENCE: 3

Gln Val Gln Leu Gln Gln Ser Gly Ala Glu Leu Ala Glu Pro Gly Ala
1               5                   10                  15

Ser Val Lys Met Ser Cys Lys Ala Ser Gly Tyr Thr Phe Ser
                20                  25                  30

<210> SEQ ID NO 4
<211> LENGTH: 14
<212> TYPE: PRT
<213> ORGANISM: Artificial Sequence
<220> FEATURE:
<223> OTHER INFORMATION: heavy chain framework region

<400> SEQUENCE: 4

Trp Val Lys Gln Arg Pro Gly Gln Gly Leu Glu Trp Ile Gly
1               5                   10

<210> SEQ ID NO 5

```
<211> LENGTH: 32
<212> TYPE: PRT
<213> ORGANISM: Artificial Sequence
<220> FEATURE:
<223> OTHER INFORMATION: heavy chain framework region

<400> SEQUENCE: 5

Lys Ala Thr Met Thr Ala Asp Thr Ser Ser Thr Ala Tyr Met Gln
1               5                   10                  15

Leu Ser Gly Leu Thr Ser Glu Asp Ser Ala Val Tyr Tyr Cys Ala Ser
            20                  25                  30

<210> SEQ ID NO 6
<211> LENGTH: 119
<212> TYPE: PRT
<213> ORGANISM: Artificial Sequence
<220> FEATURE:
<223> OTHER INFORMATION: Sequence 7 from patent US 7550142

<400> SEQUENCE: 6

Gln Val Gln Leu Val Glu Ser Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Asp Ser Val
    50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
            100                 105                 110

Thr Met Val Thr Val Ser Ser
        115

<210> SEQ ID NO 7
<211> LENGTH: 108
<212> TYPE: PRT
<213> ORGANISM: Artificial Sequence
<220> FEATURE:
<223> OTHER INFORMATION: Sequence 8 from patent US 7550142

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105
```

<210> SEQ ID NO 8
<211> LENGTH: 119
<212> TYPE: PRT
<213> ORGANISM: Artificial Sequence
<220> FEATURE:
<223> OTHER INFORMATION: Sequence 7 from patent US 7163681

<400> SEQUENCE: 8

Gln Val Gln Leu Val Glu Ser Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Asp Ser Val
    50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
            100                 105                 110

Thr Met Val Thr Val Ser Ser
        115

<210> SEQ ID NO 9
<211> LENGTH: 108
<212> TYPE: PRT
<213> ORGANISM: Artificial Sequence
<220> FEATURE:
<223> OTHER INFORMATION: Sequence 8 from patent US 7163681

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 10
<211> LENGTH: 933
<212> TYPE: PRT
<213> ORGANISM: Homo sapiens

<400> SEQUENCE: 10

Met Arg Ala Leu Ala Val Leu Ser Val Thr Leu Val Met Ala Cys Thr
1               5                   10                  15

Glu Ala Phe Phe Pro Phe Ile Ser Arg Gly Lys Glu Leu Leu Trp Gly
            20                  25                  30

-continued

```
Lys Pro Glu Glu Ser Arg Val Ser Val Leu Glu Ser Lys Arg
            35                  40                  45
Leu Val Asp Thr Ala Met Tyr Ala Thr Met Gln Arg Asn Leu Lys Lys
 50                  55                  60
Arg Gly Ile Leu Ser Pro Ala Gln Leu Leu Ser Phe Ser Lys Leu Pro
 65                  70                  75                  80
Glu Pro Thr Ser Gly Val Ile Ala Arg Ala Ala Glu Ile Met Glu Thr
                 85                  90                  95
Ser Ile Gln Ala Met Lys Arg Lys Val Asn Leu Lys Thr Gln Gln Ser
            100                 105                 110
Gln His Pro Thr Asp Ala Leu Ser Glu Asp Leu Leu Ser Ile Ile Ala
            115                 120                 125
Asn Met Ser Gly Cys Leu Pro Tyr Met Leu Pro Pro Lys Cys Pro Asn
130                 135                 140
Thr Cys Leu Ala Asn Lys Tyr Arg Pro Ile Thr Gly Ala Cys Asn Asn
145                 150                 155                 160
Arg Asp His Pro Arg Trp Gly Ala Ser Asn Thr Ala Leu Ala Arg Trp
                165                 170                 175
Leu Pro Pro Val Tyr Glu Asp Gly Phe Ser Gln Pro Arg Gly Trp Asn
                180                 185                 190
Pro Gly Phe Leu Tyr Asn Gly Phe Pro Leu Pro Pro Val Arg Glu Val
                195                 200                 205
Thr Arg His Val Ile Gln Val Ser Asn Glu Val Val Thr Asp Asp Asp
                210                 215                 220
Arg Tyr Ser Asp Leu Leu Met Ala Trp Gly Gln Tyr Ile Asp His Asp
225                 230                 235                 240
Ile Ala Phe Thr Pro Gln Ser Thr Ser Lys Ala Ala Phe Gly Gly Gly
                245                 250                 255
Ala Asp Cys Gln Met Thr Cys Glu Asn Gln Asn Pro Cys Phe Pro Ile
                260                 265                 270
Gln Leu Pro Glu Glu Ala Arg Pro Ala Ala Gly Thr Ala Cys Leu Pro
            275                 280                 285
Phe Tyr Arg Ser Ser Ala Ala Cys Gly Thr Gly Asp Gln Gly Ala Leu
            290                 295                 300
Phe Gly Asn Leu Ser Thr Ala Asn Pro Arg Gln Gln Met Asn Gly Leu
305                 310                 315                 320
Thr Ser Phe Leu Asp Ala Ser Thr Val Tyr Gly Ser Ser Pro Ala Leu
                325                 330                 335
Glu Arg Gln Leu Arg Asn Trp Thr Ser Ala Glu Gly Leu Leu Arg Val
            340                 345                 350
His Ala Arg Leu Arg Asp Ser Gly Arg Ala Tyr Leu Pro Phe Val Pro
            355                 360                 365
Pro Arg Ala Pro Ala Ala Cys Ala Pro Glu Pro Gly Ile Pro Gly Glu
            370                 375                 380
Thr Arg Gly Pro Cys Phe Leu Ala Gly Asp Gly Arg Ala Ser Glu Val
385                 390                 395                 400
Pro Ser Leu Thr Ala Leu His Thr Leu Trp Leu Arg Glu His Asn Arg
                405                 410                 415
Leu Ala Ala Ala Leu Lys Ala Leu Asn Ala His Trp Ser Ala Asp Ala
                420                 425                 430
Val Tyr Gln Glu Ala Arg Lys Val Val Gly Ala Leu His Gln Ile Ile
            435                 440                 445
Thr Leu Arg Asp Tyr Ile Pro Arg Ile Leu Gly Pro Glu Ala Phe Gln
```

```
                450             455             460
Gln Tyr Val Gly Pro Tyr Glu Gly Tyr Asp Ser Thr Ala Asn Pro Thr
465                 470                 475                 480

Val Ser Asn Val Phe Ser Thr Ala Ala Phe Arg Phe Gly His Ala Thr
                485                 490                 495

Ile His Pro Leu Val Arg Arg Leu Asp Ala Ser Phe Gln Glu His Pro
            500                 505                 510

Asp Leu Pro Gly Leu Trp Leu His Gln Ala Phe Phe Ser Pro Trp Thr
        515                 520                 525

Leu Leu Arg Gly Gly Gly Leu Asp Pro Leu Ile Arg Gly Leu Leu Ala
    530                 535                 540

Arg Pro Ala Lys Leu Gln Val Gln Asp Gln Leu Met Asn Glu Glu Leu
545                 550                 555                 560

Thr Glu Arg Leu Phe Val Leu Ser Asn Ser Thr Leu Asp Leu Ala
                565                 570                 575

Ser Ile Asn Leu Gln Arg Gly Arg Asp His Gly Leu Pro Gly Tyr Asn
            580                 585                 590

Glu Trp Arg Glu Phe Cys Gly Leu Pro Arg Leu Glu Thr Pro Ala Asp
        595                 600                 605

Leu Ser Thr Ala Ile Ala Ser Arg Ser Val Ala Asp Lys Ile Leu Asp
    610                 615                 620

Leu Tyr Lys His Pro Asp Asn Ile Asp Val Trp Leu Gly Gly Leu Ala
625                 630                 635                 640

Glu Asn Phe Leu Pro Arg Ala Arg Thr Gly Pro Leu Phe Ala Cys Leu
                645                 650                 655

Ile Gly Lys Gln Met Lys Ala Leu Arg Asp Gly Asp Trp Phe Trp Trp
            660                 665                 670

Glu Asn Ser His Val Phe Thr Asp Ala Gln Arg Arg Glu Leu Glu Lys
        675                 680                 685

His Ser Leu Ser Arg Val Ile Cys Asp Asn Thr Gly Leu Thr Arg Val
    690                 695                 700

Pro Met Asp Ala Phe Gln Val Gly Lys Phe Pro Glu Asp Phe Glu Ser
705                 710                 715                 720

Cys Asp Ser Ile Thr Gly Met Asn Leu Glu Ala Trp Arg Glu Thr Phe
                725                 730                 735

Pro Gln Asp Asp Lys Cys Gly Phe Pro Glu Ser Val Glu Asn Gly Asp
            740                 745                 750

Phe Val His Cys Glu Glu Ser Gly Arg Arg Val Leu Val Tyr Ser Cys
        755                 760                 765

Arg His Gly Tyr Glu Leu Gln Gly Arg Glu Gln Leu Thr Cys Thr Gln
    770                 775                 780

Glu Gly Trp Asp Phe Gln Pro Pro Leu Cys Lys Asp Val Asn Glu Cys
785                 790                 795                 800

Ala Asp Gly Ala His Pro Pro Cys His Ala Ser Ala Arg Cys Arg Asn
                805                 810                 815

Thr Lys Gly Gly Phe Gln Cys Leu Cys Ala Asp Pro Tyr Glu Leu Gly
            820                 825                 830

Asp Asp Gly Arg Thr Cys Val Asp Ser Gly Arg Leu Pro Arg Val Thr
        835                 840                 845

Trp Ile Ser Met Ser Leu Ala Ala Leu Leu Ile Gly Gly Phe Ala Gly
    850                 855                 860

Leu Thr Ser Thr Val Ile Cys Arg Trp Thr Arg Thr Gly Thr Lys Ser
865                 870                 875                 880
```

```
Thr Leu Pro Ile Ser Glu Thr Gly Gly Thr Pro Glu Leu Arg Cys
                885                 890                 895

Gly Lys His Gln Ala Val Gly Thr Ser Pro Gln Arg Ala Ala Ala Gln
                900                 905                 910

Asp Ser Glu Gln Glu Ser Ala Gly Met Glu Gly Arg Asp Thr His Arg
            915                 920                 925

Leu Pro Arg Ala Leu
        930
```

<210> SEQ ID NO 11
<211> LENGTH: 120
<212> TYPE: PRT
<213> ORGANISM: Homo sapiens

<400> SEQUENCE: 11

```
Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp Arg Phe His
        35                  40                  45

Ala Thr Ser Ala Asp Cys Cys Ile Ser Tyr Thr Pro Arg Ser Ile Pro
    50                  55                  60

Cys Ser Leu Leu Glu Ser Tyr Phe Glu Thr Asn Ser Glu Cys Ser Lys
65                  70                  75                  80

Pro Gly Val Ile Phe Leu Thr Lys Lys Gly Arg Arg Phe Cys Ala Asn
                85                  90                  95

Pro Ser Asp Lys Gln Val Gln Val Cys Val Arg Met Leu Lys Leu Asp
            100                 105                 110

Thr Arg Ile Lys Thr Arg Lys Asn
        115                 120
```

<210> SEQ ID NO 12
<211> LENGTH: 384
<212> TYPE: PRT
<213> ORGANISM: Homo sapiens

<400> SEQUENCE: 12

```
Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140
```

```
Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Ser Pro Gln Pro Ala Thr
            340                 345                 350

Tyr Thr Cys Val Val Ser His Glu Asp Ser Arg Thr Leu Leu Asn Ala
        355                 360                 365

Ser Arg Ser Leu Glu Val Ser Tyr Val Thr Asp His Gly Pro Met Lys
    370                 375                 380

<210> SEQ ID NO 13
<211> LENGTH: 693
<212> TYPE: PRT
<213> ORGANISM: Homo sapiens

<400> SEQUENCE: 13

Met Ala Ala Leu Gly Val Gln Ser Ile Asn Trp Gln Thr Ala Phe Asn
1               5                   10                  15

Arg Gln Ala His His Thr Asp Lys Phe Ser Ser Gln Glu Leu Ile Leu
            20                  25                  30

Arg Arg Gly Gln Asn Phe Gln Val Leu Met Ile Met Asn Lys Gly Leu
        35                  40                  45

Gly Ser Asn Glu Arg Leu Glu Phe Ile Val Ser Thr Gly Pro Tyr Pro
    50                  55                  60

Ser Glu Ser Ala Met Thr Lys Ala Val Phe Pro Leu Ser Asn Gly Ser
65                  70                  75                  80

Ser Gly Gly Trp Ser Ala Val Leu Gln Ala Ser Asn Gly Asn Thr Leu
                85                  90                  95

Thr Ile Ser Ile Ser Ser Pro Ala Ser Ala Pro Ile Gly Arg Tyr Thr
            100                 105                 110

Met Ala Leu Gln Ile Phe Ser Gln Gly Gly Ile Ser Ser Val Lys Leu
        115                 120                 125

Gly Thr Phe Ile Leu Leu Phe Asn Pro Trp Leu Asn Val Asp Ser Val
```

```
              130                 135                 140
Phe Met Gly Asn His Ala Glu Arg Glu Tyr Val Gln Glu Asp Ala
145                 150                 155                 160

Gly Ile Ile Phe Val Gly Ser Thr Asn Arg Ile Gly Met Ile Gly Trp
                165                 170                 175

Asn Phe Gly Gln Phe Glu Glu Asp Ile Leu Ser Ile Cys Leu Ser Ile
                180                 185                 190

Leu Asp Arg Ser Leu Asn Phe Arg Arg Asp Ala Ala Thr Asp Val Ala
                195                 200                 205

Ser Arg Asn Asp Pro Lys Tyr Val Gly Arg Val Leu Ser Ala Met Ile
210                 215                 220

Asn Ser Asn Asp Asp Asn Gly Val Leu Ala Gly Asn Trp Ser Gly Thr
225                 230                 235                 240

Tyr Thr Gly Gly Arg Asp Pro Arg Ser Trp Asn Gly Ser Val Glu Ile
                245                 250                 255

Leu Lys Asn Trp Lys Lys Ser Gly Phe Ser Pro Val Arg Tyr Gly Gln
                260                 265                 270

Cys Trp Val Phe Ala Gly Thr Leu Asn Thr Ala Leu Arg Ser Leu Gly
                275                 280                 285

Ile Pro Ser Arg Val Ile Thr Asn Phe Asn Ser Ala His Asp Thr Asp
                290                 295                 300

Arg Asn Leu Ser Val Asp Val Tyr Tyr Asp Pro Met Gly Asn Pro Leu
305                 310                 315                 320

Asp Lys Gly Ser Asp Ser Val Trp Asn Phe His Val Trp Asn Glu Gly
                325                 330                 335

Trp Phe Val Arg Ser Asp Leu Gly Pro Ser Tyr Gly Gly Trp Gln Val
                340                 345                 350

Leu Asp Ala Thr Pro Gln Glu Arg Ser Gln Gly Val Phe Gln Cys Gly
                355                 360                 365

Pro Ala Ser Val Ile Gly Val Arg Glu Gly Asp Val Gln Leu Asn Phe
                370                 375                 380

Asp Met Pro Phe Ile Phe Ala Glu Val Asn Ala Asp Arg Ile Thr Trp
385                 390                 395                 400

Leu Tyr Asp Asn Thr Thr Gly Lys Gln Trp Lys Asn Ser Val Asn Ser
                405                 410                 415

His Thr Ile Gly Arg Tyr Ile Ser Thr Lys Ala Val Gly Ser Asn Ala
                420                 425                 430

Arg Met Asp Val Thr Asp Lys Tyr Lys Tyr Pro Glu Gly Ser Asp Gln
                435                 440                 445

Glu Arg Gln Val Phe Gln Lys Ala Leu Gly Lys Leu Lys Pro Asn Thr
450                 455                 460

Pro Phe Ala Ala Thr Ser Ser Met Gly Leu Thr Glu Glu Gln Glu
465                 470                 475                 480

Pro Ser Ile Ile Gly Lys Leu Lys Val Ala Gly Met Leu Ala Val Gly
                485                 490                 495

Lys Glu Val Asn Leu Val Leu Leu Leu Lys Asn Leu Ser Arg Asp Thr
                500                 505                 510

Lys Thr Val Thr Val Asn Met Thr Ala Trp Thr Ile Ile Tyr Asn Gly
                515                 520                 525

Thr Leu Val His Glu Val Trp Lys Asp Ser Ala Thr Met Ser Leu Asp
                530                 535                 540

Pro Glu Glu Glu Ala Glu His Pro Ile Lys Ile Ser Tyr Ala Gln Tyr
545                 550                 555                 560
```

```
Glu Lys Tyr Leu Lys Ser Asp Asn Met Ile Arg Ile Thr Ala Val Cys
                565                 570                 575

Lys Val Pro Asp Glu Ser Glu Val Val Glu Arg Asp Ile Ile Leu
            580                 585                 590

Asp Asn Pro Thr Leu Thr Leu Glu Val Leu Asn Glu Ala Arg Val Arg
            595                 600                 605

Lys Pro Val Asn Val Gln Met Leu Phe Ser Asn Pro Leu Asp Glu Pro
        610                 615                 620

Val Arg Asp Cys Val Leu Met Val Glu Gly Ser Gly Leu Leu Leu Gly
625                 630                 635                 640

Asn Leu Lys Ile Asp Val Pro Thr Leu Gly Pro Lys Glu Gly Ser Arg
                645                 650                 655

Val Arg Phe Asp Ile Leu Pro Ser Arg Ser Gly Thr Lys Gln Leu Leu
            660                 665                 670

Ala Asp Phe Ser Cys Asn Lys Phe Pro Ala Ile Lys Ala Met Leu Ser
            675                 680                 685

Ile Asp Val Ala Glu
    690

<210> SEQ ID NO 14
<211> LENGTH: 288
<212> TYPE: PRT
<213> ORGANISM: Homo sapiens

<400> SEQUENCE: 14

Met Lys Asp Arg Thr Gln Glu Leu Arg Thr Ala Lys Asp Ser Asp Asp
1               5                   10                  15

Asp Asp Asp Val Ala Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
```

```
                225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Cys Cys
                260                 265                 270

Val Ile Leu Gly Ile Val Ile Ala Ser Thr Val Gly Ile Phe Ala
                275                 280                 285

<210> SEQ ID NO 15
<211> LENGTH: 234
<212> TYPE: PRT
<213> ORGANISM: Homo sapiens

<400> SEQUENCE: 15

Met Ser Cys Ile Asn Leu Pro Thr Val Leu Pro Gly Ser Pro Ser Lys
1               5                   10                  15

Thr Arg Gly Gln Ile Gln Val Ile Leu Gly Pro Met Phe Ser Gly Lys
                20                  25                  30

Ser Thr Glu Leu Met Arg Arg Val Arg Arg Phe Gln Ile Ala Gln Tyr
            35                  40                  45

Lys Cys Leu Val Ile Lys Tyr Ala Lys Asp Thr Arg Tyr Ser Ser Ser
    50                  55                  60

Phe Cys Thr His Asp Arg Asn Thr Met Glu Ala Leu Pro Ala Cys Leu
65                  70                  75                  80

Leu Arg Asp Val Ala Gln Glu Ala Leu Gly Val Ala Val Ile Gly Ile
                85                  90                  95

Asp Glu Gly Gln Phe Phe Pro Asp Ile Val Glu Phe Cys Glu Ala Met
                100                 105                 110

Ala Asn Ala Gly Lys Thr Val Ile Val Ala Ala Leu Asp Gly Thr Phe
            115                 120                 125

Gln Arg Lys Pro Phe Gly Ala Ile Leu Asn Leu Val Pro Leu Ala Glu
        130                 135                 140

Ser Val Val Lys Leu Thr Ala Val Cys Met Glu Cys Phe Arg Glu Ala
145                 150                 155                 160

Ala Tyr Thr Lys Arg Leu Gly Thr Glu Lys Glu Val Glu Val Ile Gly
                165                 170                 175

Gly Ala Asp Lys Tyr His Ser Val Cys Arg Leu Cys Tyr Phe Lys Lys
                180                 185                 190

Ala Ser Gly Gln Pro Ala Gly Pro Asp Asn Lys Glu Asn Cys Pro Val
            195                 200                 205

Pro Gly Lys Pro Gly Glu Ala Val Ala Ala Arg Lys Leu Phe Ala Pro
        210                 215                 220

Gln Gln Ile Leu Gln Cys Ser Pro Ala Asn
225                 230

<210> SEQ ID NO 16
<211> LENGTH: 155
<212> TYPE: PRT
<213> ORGANISM: Homo sapiens

<400> SEQUENCE: 16

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
```

```
                    35                  40                  45
Leu Asn Ile His Asn Arg Asn Thr Asn Thr Asn Pro Lys Arg Ser Ser
 50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 17
<211> LENGTH: 221
<212> TYPE: PRT
<213> ORGANISM: Homo sapiens

<400> SEQUENCE: 17

Met Pro Val Met Arg Leu Phe Pro Cys Phe Leu Gln Leu Leu Ala Gly
  1               5                  10                  15

Leu Ala Leu Pro Ala Val Pro Pro Gln Gln Trp Ala Leu Ser Ala Gly
                 20                  25                  30

Asn Gly Ser Ser Glu Val Glu Val Pro Phe Gln Glu Val Trp Gly
             35                  40                  45

Arg Ser Tyr Cys Arg Ala Leu Glu Arg Leu Val Asp Val Val Ser Glu
 50                  55                  60

Tyr Pro Ser Glu Val Glu His Met Phe Ser Pro Ser Cys Val Ser Leu
 65                  70                  75                  80

Leu Arg Cys Thr Gly Cys Cys Gly Asp Glu Asn Leu His Cys Val Pro
                 85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg His Ser Pro Gly Arg Gln Ser Pro Asp Met Pro Gly Asp
    130                 135                 140

Phe Arg Ala Asp Ala Pro Ser Phe Leu Pro Pro Arg Arg Ser Leu Pro
145                 150                 155                 160

Met Leu Phe Arg Met Glu Trp Gly Cys Ala Leu Thr Gly Ser Gln Ser
                165                 170                 175

Ala Val Trp Pro Ser Ser Pro Val Pro Glu Glu Ile Pro Arg Met His
            180                 185                 190

Pro Gly Arg Asn Gly Lys Lys Gln Gln Arg Lys Pro Leu Arg Glu Lys
        195                 200                 205

Met Lys Pro Glu Arg Cys Gly Asp Ala Val Pro Arg Arg
    210                 215                 220

<210> SEQ ID NO 18
<211> LENGTH: 11
<212> TYPE: PRT
<213> ORGANISM: Artificial Sequence
<220> FEATURE:
```

```
<223> OTHER INFORMATION: heavy chain framework region

<400> SEQUENCE: 18

Trp Gly Gln Gly Thr Ser Val Thr Val Ser Ser
1               5                   10
```

The invention claimed is:

1. A method of treating colorectal cancer and/or metastases thereof in a human subject, comprising:
   determining a level of STX1A comprising the amino acid sequence of SEQ ID NO: 14 in at least one body fluid of the subject prior to administering at least one pan αv integrin inhibitor comprising Abituzumab, wherein:
   the level of STX1A present in the at least one body fluid of the subject is determined to be at least 5% higher than a median level of STX1A comprising SEQ ID NO: 14 determined for the at least one body fluid from cancer patients having colorectal cancer and/or metastases thereof;
   administering to said subject the at least one pan αv integrin inhibitor comprising Abituzumab, wherein said Abituzumab comprises:
   a light chain variable region (VL) complementarity determining region (CDR)1 comprising the sequence of amino acids 24 to 34 of SEQ ID NO: 1, VL CDR2 comprising the sequence of amino acids 50 to 56 of SEQ ID NO: 1, and VL CDR3 comprising the sequence of amino acids 89 to 97 of SEQ ID NO: 1; and
   a heavy chain comprising the sequence of SEQ ID NO: 2;
   wherein said body fluid is selected from the group consisting of blood plasma, blood serum and whole blood.

2. The method according to claim 1, wherein said at least one pan αv integrin inhibitor comprising Abituzumab is administered to said subject amount of 100 mg to 3000 mg per month.

3. The method according to claim 1, wherein an amount of 500 to 2000 mg of Abituzumab is administered to said subject every week, every second week, or every fourth week.

4. The method according to claim 1, wherein an amount of 500 mg +/− 10% of Abituzumab, 750 mg +/− 10% of Abituzumab, thousand milligrams +/− 10% of Abituzumab, or 1500 mg +/− 10% of Abituzumab is administered to the subject every week, every second week, or every fourth week.

5. The method according to claim 1, wherein said Abituzumab comprises:
   a light chain, wherein the light chain has at least 95% amino acid identity to SEQ ID NO: 1; and
   wherein any change in the amino acid sequence of SEQ ID NO: 1 is in a framework region of the light chain.

6. The method according to claim 5, wherein a constant region of the light chain has at least 98% amino acid identity to a constant region of SEQ ID NO: 1.

* * * * *